US007030210B2

(12) United States Patent
Cleaver et al.

(10) Patent No.: US 7,030,210 B2
(45) Date of Patent: Apr. 18, 2006

(54) MATERIALS AND METHODS FOR DETECTION AND QUANTITATION OF AN ANALYTE

(75) Inventors: Brian D. Cleaver, Archer, FL (US); Mike L. Green, Gainesville, FL (US)

(73) Assignee: Equitech Laboratories, Inc., Alachua, FL (US)

( * ) Notice: Subject to any disclaimer, the term of this patent is extended or adjusted under 35 U.S.C. 154(b) by 276 days.

(21) Appl. No.: 10/334,583

(22) Filed: Dec. 31, 2002

(65) Prior Publication Data
US 2003/0104484 A1 Jun. 5, 2003

Related U.S. Application Data

(63) Continuation of application No. 09/660,979, filed on Sep. 13, 2000, now Pat. No. 6,500,629.

(60) Provisional application No. 60/153,627, filed on Sep. 13, 1999.

(51) Int. Cl.
*A61K 38/00* (2006.01)
*C07K 2/00* (2006.01)

(52) U.S. Cl. .................. 530/300; 530/350; 435/7.1; 436/86; 436/501

(58) Field of Classification Search .............. 530/300, 530/350; 435/7.1; 436/86, 501
See application file for complete search history.

(56) References Cited

U.S. PATENT DOCUMENTS

| | | | |
|---|---|---|---|
| 4,228,240 A | 10/1980 | Dawson et al. | |
| 4,323,536 A | 4/1982 | Columbus | |
| 4,361,537 A | 11/1982 | Deutsch et al. | |
| 4,376,110 A | 3/1983 | David et al. | |
| 4,623,461 A | 11/1986 | Hossom et al. | |
| 4,855,240 A | 8/1989 | Rosenstein et al. | |
| 4,931,385 A | 6/1990 | Blocker et al. | |
| 4,943,522 A | 7/1990 | Eisinger et al. | |
| 5,460,976 A | 10/1995 | O'Connor | |
| 5,576,195 A | 11/1996 | Robinson et al. | |
| 5,766,961 A | 6/1998 | Pawlak et al. | |
| 5,770,460 A | 6/1998 | Pawlak et al. | |
| 5,843,726 A | 12/1998 | Lee | |

FOREIGN PATENT DOCUMENTS

WO    WO 99/18124    4/1999

OTHER PUBLICATIONS

McDowell et al., Changes in equine endometrial oestrogen receptor alpha . . . , Journal of Reproduction and Fertility, Sep. 1, 1999, 117, 135-142.*
Mosselman et al., ERbeta: identification and characterization of a novel human estrogen receptor., FEBS Letters, 392, 1996, 49-53.*
GenCore version 5.1.6 search results for SEQ ID No.: 1 dated Jan. 14, 2005, p. 1 -ESR1_ HORSE.*
Adams, M.H. et al. "Molecular Cloning of Estrogen and Progesterone Receptors From Equine" *Biology of Reproduction*, 1997, p. 153, vol. 56 (suppl. 1), abstract only, XP-000998725.
Allen, W.R. et al. (1995) "Serial Measurement of Peripheral Oestrogen and Progesterone Concentrations in Oestrous Mares to Determine Optimum Mating Time and Diagnose Ovulation" *Equine Veterinary Journal*, 1995, pp. 460-464, vol. 27, No. 6.
Ball, B.A. et al. "Pregnancy Rates at Days 2 and 14 and Estimated Embryonic Loss Rates Prior to Day 14 in Normal and Subfertile Mares" *Theriogenology*, 1986, pp. 611-619, vol. 26, No. 5.
Bazer, F.W. et al. "Role of Conceptus Secretory Products in Establishment of Pregnancy" *J. Reprod. Fert.*, 1986, pp. 841-850, vol. 76.
Davis, S.D. et al. "Intra-follicular and Peripheral Steroid Characteristics During Vernal Transition in the Pony Mare" *J. Reprod. Fert. Suppl.*, 1991, pp. 333-340, vol. 44.
Diskin, M.G. et al. "Fertilization and Embryonic Mortality Rates in Beef Heifers After Artificial Insemination" *J. Reprod. Fert.*, 1980, pp. 463-468, vol. 59, No. 2.
Ekena, K. et al. (1996) "Identification of Amino Acids in the Hormone Binding Domain of the Human Estrogen Receptor Important in Estrogen Binding" *J. Biol. Chem.*, 1996, pp. 20053-20059, vol. 271, No. 33.
Garrett, S.D. et al. "A Nonisotopic Estrogen Receptor-Based Assay to Detect Estrogenic Compounds" *Nature Biotechnology*, 1999, pp. 1219-1222. vol. 17.
Ginther, O.J. "Embryonic Loss" *Ultrasonic Imaging and Reproductive Events in the Mare Equiservices*, 1986, pp. 253-282, Cross Plains, Wisconsin.
Ginther, O.J. "Sexual Behavior" In: *Reproductive Biology of the Mare*, 1992, pp. 77-83, McNaughton and Gunn, Ann Arbor, Michigan.

(Continued)

*Primary Examiner*—Long V. Le
*Assistant Examiner*—Lisa V. Cook
(74) *Attorney, Agent, or Firm*—Saliwanchik, Lloyd &Saliwanchik

(57) ABSTRACT

The subject invention pertains to methods and materials for accurately assessing the presence or absence of analytes of interest in samples, particularly in physiological samples. The subject invention involves utilizing a ligand binding domain (LBD) of a receptor to selectively capture the analyte target specific for that LBD. In one embodiment, the receptor is a protein or polypeptide. The ligand binding domain is allowed to react with a sample and the presence or amount of ligand (i.e., target analyte) bound by the LBD is determined. Suitable analytes include soluble analytes such as hormones, enzymes, lipoproteins, bacterial or viral antigens, immunoglobulines, lymphokines, cytokines, drugs, soluble cancer antigens, and the like. The methods of the present invention can be performed in both liquid-phase and solid-phase.

1 Claim, 9 Drawing Sheets

OTHER PUBLICATIONS

Greene, G.L. et al. "Monoclonal Antibodies to Human Estrogen Receptor" *Proc. Natl. Acad. USA*, 1980, pp. 5115-5119, vol. 77, No. 9.

Hanly, S. "Prenatal Mortality in Farm Animals" *J. Reprod. Fertil.*, 1961, pp. 182-194, vol. 2.

Jeffcoat, L.B. "Observations on Parturition in Crossbred Pony Mares" *Equine Vet. J.*, 1972, pp. 209-216, Vo. 4.

King, W.A. "Chromosome Abnormalities and Pregnancy Failure in Domestic Animals" *Adv. Vet. Sci. Comp. Med.*, 1990, pp. 229-250, vol. 34.

Lipner, H. "Mechanism of Mammalian Ovulation" In: *The Physiology of Reproduction*, 1988, pp. 447-476, E. Knobil and J. Neill, eds., Raven Press, Ltd., New York.

Munro, C.J. et al. "Non-Radiometric Methods for Immunoassay of Steroid Hormones" In: *Non-Radiometric Assays: Technology and Application in Polypeptide and Steroid Hormone Detection*, 1988, pp. 289-323, B.D. Albertson and F.P. Haseltine eds., Alan R. Liss, Inc., New York.

Munro, C.J. et al. "Development of a Microtitre Plate Enzyme Immunoassay for the Determination of Progesterone" *J. Endocr.*, 1984, pp. 41-49, vol. 101, No. 1.

Pattison, M.L. et al. "Luteinizing Hormone and Estradiol in Peripheral Blood of Mares During Estrous Cycle" *Biol. Reprod.*, 1974, pp. 245-250, vol. 11, No. 3.

Nancarrow, C.D. "Embryonic Mortality in the Ewe and Doe" In: *Embryonic Mortality in Domestic Species*. 1994, pp. 79-90, M.T. Zavy and R.D. Geisert, eds., CRC Press, Inc., Boca Raton, Florida.

Pope, W.F. et al. "Factors Affecting the Survival of Pig Embryos" *Theriogenology*, 1985, pp. 91-105, vol. 23, No. 1.

Rehmann, K. et al. "Applicability of a Yeast Oestrogen Screen for the Detection of Oestrogen-Like Activities in Environmental Samples" *Chemosphere*, 1999, pp. 3303-3312, vol. 38, No. 14.

Salomonsson, M.J. et al. "The Human Estrogen Receptor Hormone Binding Domain Dimerizes Independently of Ligand Activation" *J. Steroid Biochem. Molec. Biol.*, 1994, pp. 447-452, vol. 48, No. 5.

Sambrook, J. et al. "Plasmid Vectors" In: *Molecular Cloning: A Laboratory Manual*, 2d Edition, 1989, pp. 1.82-1.104. Cold Spring Harbor Laboratory Press, Cold Spring Harbor, New York.

Scatchard, G. "The Attractions of Proteins for Small Molecules and Ions" *Ann. NY Acad. Sci.*, 1949, pp. 660-672, vol. 51.

Seielstad, D.A. et al. "Molecular Characterization by Mass Spectrometry of the Human Estrogen Receptor Ligand-Binding Domain Expressed in *Eschericia coli*" *Mol. Endocrinol.*, 1995, pp. 647-658, vol. 9, No. 6.

Sharp, D.C. et al. "Role of Photoperiod in Regulating Reproduction in Mares: Basic and Practical Aspects" In: *Current Therapy in Large Animal Theriogenology*, 1997, pp. 71-77, R.S. Youngquist, ed., WB Saunders, Philadelphia, PA.

Strauss, S.S. et al. "Localization of Gonadotrophin-Releasing Hormone (GnRH) in the Hypothalamus of Ovariectomized Pony Mares by Season" *J. Reprod. Fertil., Suppl.*, 1979, pp. 123-129, vol. 27.

Tanenbaum, D.M. et al. "Crystallographic Comparison of the Estrogen and Progesterone Receptor's Ligand Binding Domains" *Proc. Natl. Acad. Sci. USA*, 1998, pp. 5998-6003, vol. 95, No. 11.

TBH Market Watch, Foaling Dates, Aug. 21, 1997, pp. 1 and 11.

Tucker, K.E. et al. "Does Resumption of Follicular Estradiol Synthesis During Vernal Transition in Mares Involve a Shift in Steroidogenic Pathways?" *Biology of Reproduction, Supplement*, 1993, p. 188, vol. 48, abstract only, XP-000998724.

Villahoz, M.D. et al. "Some Observations on Early Embryonic Death in Mares" *Theriogenology*, 1985, pp. 915-924, vol. 23, No. 6.

Wrenn, C.K. et al. "Structure-Function Analysis of the Hormone Binding Domain of the Human Estrogen Receptor by Region-Specific Mutagenesis and Phenotypic Screening in Yeast" *J. Biol. Chem.*, 1993, pp. 24089-24098, vol. 268, No. 32.

Yoh-Ichi, M. et al. "Fertility in the Mares with High Levels of Progesterone at the Mating" *Animal Science Journal*, 2000, pp. J311-J317, vol. 71, No. 9, abstract only, XP-002167533.

\* cited by examiner

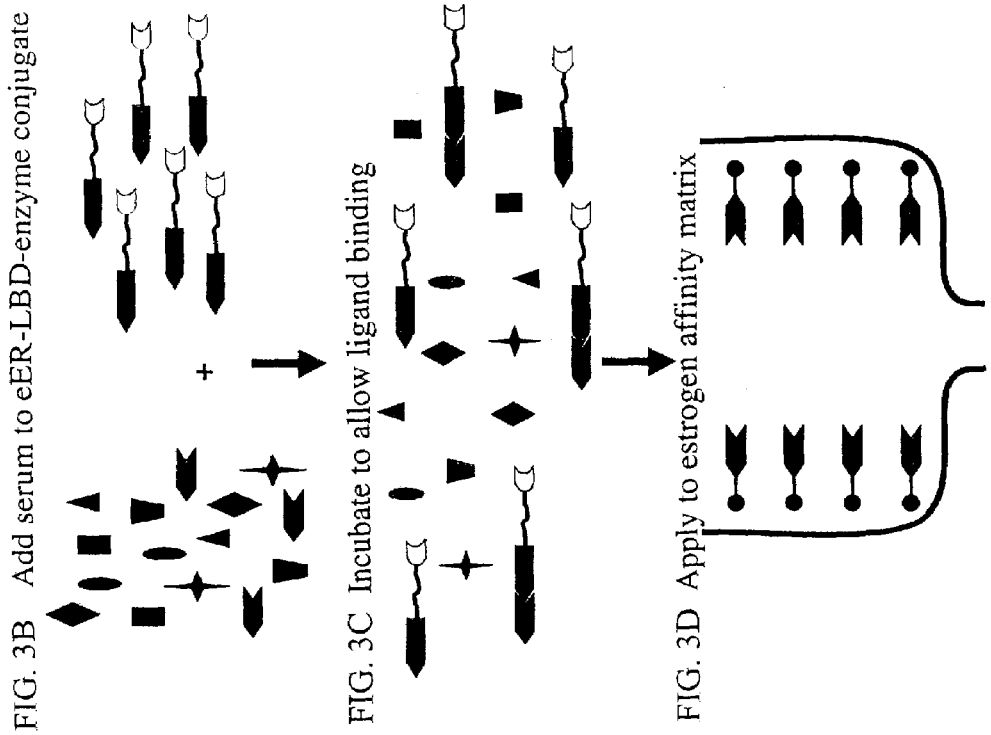

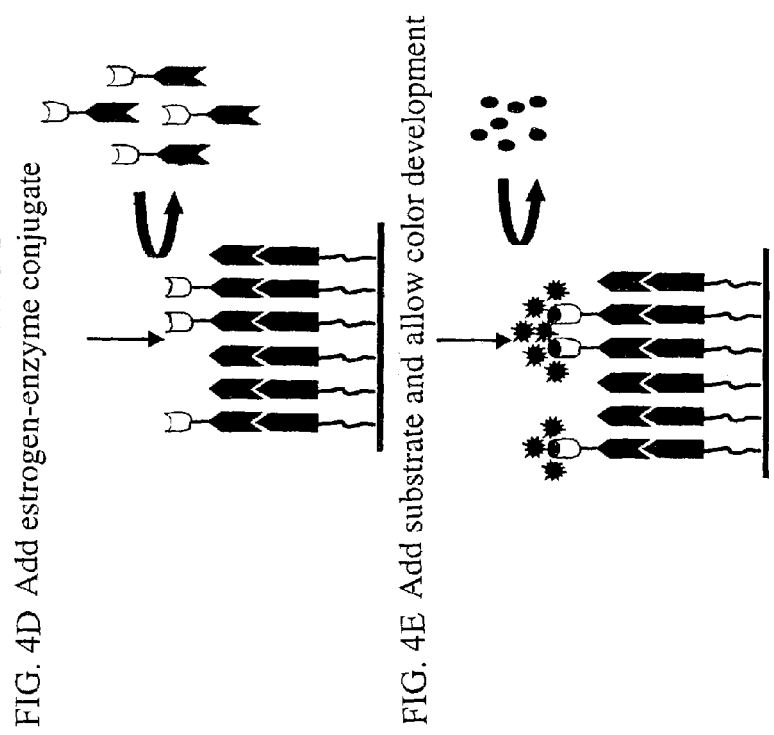
FIG. 4D Add estrogen-enzyme conjugate
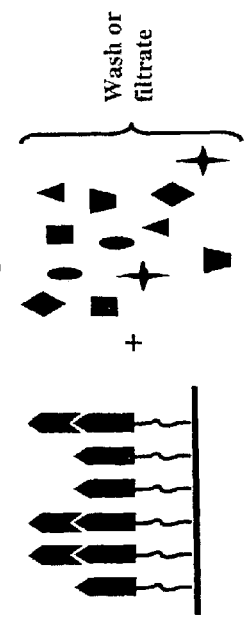
FIG. 4E Add substrate and allow color development
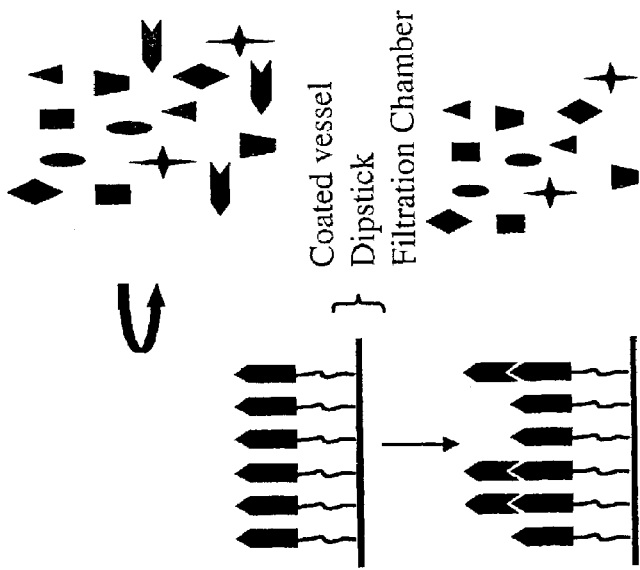
FIG. 4B Incubate serum with solid-phase eER-LBD
FIG. 4C Evacuate and wash solid-phase eER-LBD

SEQUENCE LISTING

```
<160> NUMBER OF SEQ ID NOS: 1

<210> SEQ ID NO 1
<211> LENGTH: 264
<212> TYPE: PRT
<213> ORGANISM: Equus

<400> SEQUENCE: 1

Thr Lys Lys Ile Ser Pro Val Leu Ser Leu Thr Ala Glu Gln Met Ile
1               5                   10                  15

Ser Ala Leu Leu Asp Ala Glu Pro Pro Val Leu Tyr Ser Glu Tyr Asp
                20                  25                  30

Ala Thr Arg Pro Phe Asn Glu Ala Ser Met Met Gly Leu Leu Thr Asn
            35                  40                  45

Leu Ala Asp Arg Glu Leu Val His Met Ile Asn Trp Ala Lys Arg Val
    50                  55                  60

Pro Gly Phe Val Asp Leu Ser Leu His Asp Gln Val His Leu Leu Glu
65                  70                  75                  80

Cys Ala Trp Leu Glu Ile Leu Met Ile Gly Leu Val Trp Arg Ser Met
                85                  90                  95

Glu His Pro Gly Lys Leu Leu Phe Ala Pro Asn Leu Leu Leu Asp Arg
                100                 105                 110

Asn Gln Gly Lys Cys Val Glu Gly Met Val Glu Ile Phe Asp Met Leu
            115                 120                 125

Leu Ala Thr Ser Ser Arg Leu Arg Met Met Asn Leu Gln Gly Glu Glu
    130                 135                 140
```

```
Phe Val Cys Leu Lys Ser Ile Ile Leu Leu Asn Ser Gly Val Tyr Thr
145                 150                 155                 160

Phe Leu Ser Ser Thr Leu Lys Ser Leu Glu Glu Lys Asp His Ile His
                165                 170                 175

Arg Val Leu Asp Lys Met Thr Asp Thr Leu Ile His Leu Met Ala Lys
                180                 185                 190

Ala Gly Leu Thr Leu Gln Gln His Arg Arg Leu Ala Gln Leu Leu Leu
            195                 200                 205

Ile Leu Ser His Ile Arg His Met Ser Asn Lys Gly Met Glu His Leu
        210                 215                 220

Tyr Ser Met Lys Cys Lys Asn Val Val Pro Leu Tyr Asp Leu Leu Leu
225                 230                 235                 240

Glu Met Leu Asp Ala His Arg Leu His Ala Pro Ala Asn His Gly Gly
                245                 250                 255

Ala Pro Met Glu Glu Thr Asn Gln
                260
```

MATERIALS AND METHODS FOR DETECTION AND QUANTITATION OF AN ANALYTE

CROSS-REFERENCE TO A RELATED APPLICATIONS

This application is a continuation of U.S. application Ser. No. 09/660,979, filed Sep. 13, 2000, now U.S. Pat. No. 6,500,629, which claims the benefit of U.S. Provisional Application No. 60/153,627, filed Sep. 13, 1999.

BACKGROUND OF THE INVENTION

There are a number of assay systems available for detection and quantitation of analytes, particularly analytes of biological interest. Current assay systems include enzyme immunoassay (EIA), radioimmunoassay (RIA), and enzyme linked immunosorbent assay (ELISA). Among the analytes frequently assayed with such systems are: 1) hormones, such as human chorionic gonadotropin (hCG), frequently assayed in urine as a marker of human pregnancy; 2) antigens, particularly antigens specific to bacterial, viral, and protozoan pathogens, such as Streptococcus and hepatitis virus; 3) antibodies, particularly antibodies induced as a result of infection with pathogens, such as antibody to the bacterium *Heliobacter pylori* and to human immunodeficiency virus (HIV); 4) enzymes, such as aspartite aminotransferase, lactate dehydrogenase, alkaline phosphatase, and glutamate dehydrogenase, frequently assayed as indicators of physiological function and tissue damage; 5) other proteins, such as hemoglobin, frequently assayed in determinations of fecal occult blood, an early indicator of gastrointestinal disorders such as colon cancer; 6) drugs, both therapeutic drugs, such as antibiotics, tranquilizers and anticonvulsants, and illegal drugs of abuse, such as cocaine, heroine, and marijuana; and 7) environmental pollutants such as pesticides and aromatic hydrocarbons and vitamins.

Such systems are frequently used by physicians and medical technicians for rapid in-office diagnosis and therapeutic monitoring of a variety of conditions and disorders. They are also increasingly used by patients themselves for at-home or on-site monitoring of such conditions and disorders.

Among the most popular of such assay systems are immunoassays, which depend on the specific interaction between an antigen or hapten and a corresponding antibody. The use of immunoassays as a means of testing for the presence and/or amount of clinically important molecules has been known for some time. As early as 1956, J. M. Singer reported the use of an immune-based latex agglutination test for detecting a factor associated with rheumatoid arthritis (Singer et al., 1956).

Development of the first radioimmunoassay by Rosalyn Yalow and Sol Berson (1959) set the stage for measurement of a wide variety of hormones in biological fluids by binding the hormone specifically and with high affinity to antibodies developed in animals against the hormone in question. The assay developed by Drs. Yalow and Berson employed antibodies formed against the protein hormone, insulin, and utilized a radiolabeled form of insulin as the marker, or "reporter" hormone. Antibodies became a useful way to "capture" a specific hormone from biological fluids and under conditions of constant antibody concentration and with some easily detected source of labeled hormone (usually radioactively labeled; hence the name "radioimmunoassay") the amount of hormone "captured" from the biological fluid could be quantified by comparison to known concentrations of the hormone in similar conditions. In practice of the art, known amounts of (unlabeled) hormone, (insulin in the example) were allowed to compete for binding to the antibody with a known and fixed amount of $I^{131}$ labeled insulin. The radiolabeled form of hormone, and the amount of antibody were held constant while the amount of unlabeled hormone was varied. This was the basis of a "standard curve" from which the amount of radioactive label that bound to the antibody varied inversely with the amount of unlabeled hormone. Comparison of the mass of unlabeled hormone required to displace a given amount of labeled hormone could then be used to estimate mass of an sample hormone. Separation of the fractions which were unreacted with the antibody (unbound) was carried out by a variety of chemical separation methods. In the original teaching of Yalow and Berson (1959), separation of the antibody-bound fractions of insulin from the unbound (free) fractions of insulin was carried by electrophoresis. Subsequent to their report, many means of separating bound from free fractions have been utilized, including column chromatography, salt or organic solvent precipitation of the protein (antibody), double antibody (in which the gamma globulin fraction of the species immunized against the hormone is then introduced to a different species to create an anti-antibody, or second antibody, and solid phase, in which the antibody is held by electrostatic forces to a solid interphase such as the inner wall of a test tube, flat disc, or elongate stick (dipstick) and separation of bound from free requires simple physical separation of the solid phase from the liquid phase containing the free fractions. A variant of the technique of radioimmunoassay involved coupling small, non-immunogenic molecules to larger, highly immunogenic molecules, such as bovine serum albumen (BSA), thyroglobulin (TG), or keyhole limpet hemocyanin (KLH) and stimulation of antibodies that recognized the smaller, non-immunogenic, portion of the hapten molecule. This modification of the technique permitted quantification of small hormones, such as steroids and prostaglandins.

While radioimmunoassay is a very useful tool for conducting research and for certain clinical applications, it has several drawbacks as far as practical management of endocrine or other hormonal states. A major drawback is the use of an antibody as a "capture protein." Development of polyclonal antibodies is accomplished by administering the hormone to an animal that regards it as foreign and develops antibodies against it. The process is very much trial and error and involves the use of a number of animals and screening of the antibody before determination of its usefulness. Once an ideal polyclonal antibody preparation has been obtained, the animal's plasma must be harvested and husbanded carefully, for once the animal dies, the supply of that particular antibody is lost forever.

The act of mounting an immune attack against a foreign protein and producing antibodies is actually a mixture, or collection of antibodies (hence the term "polyclonal antibody"), each of which is directed against a particular amino acid sequence called an epitope. A refinement of this process involves the production of monoclonal antibodies. Monoclonal antibodies are derived by collecting individual spleen cells from animals immunized by administration of a foreign protein and culturing the lymphocytes in vitro. The cells are then screened to determine their binding characteristics, and those cells that possess appropriate binding are then cloned and maintained as an antibody-specific, continuous cell line. Thus, once appropriate cell cultures are obtained, they may be kept essentially indefinitely, thereby obviating one of the negative aspects of polyclonal antibodies.

However, monoclonal antibodies also have some drawbacks. For one thing, they are so specific as to be a detriment in some cases. Monoclonal antibodies are directed against amino acid sequences (epitopes) that are often common features of the tertiary structure of proteins. In this case the monoclonal antibodies are really not specific as one might believe at first. This drawback can be overcome by very stringent screening and validation of the assays utilizing monoclonal antibodies, but greater effort is often required. Additionally, monoclonal antibodies tend to be monovalent, which may restrict hierarchical or sandwich type coupling to other molecules for the purpose of separation or of amplification of the reporter signal.

Immunoassays fall into two principal categories: "sandwich" and "competitive," according to the nature of the antigen-antibody complex to be detected and the sequence of reactions required to produce that complex. Generally, the sandwich immunoassay calls for mixing the sample that may contain the analyte to be assayed with antibodies to the analyte. These antibodies are mobile and typically are linked to a detectable label or a disclosing reagent, such as dyed latex or a radioisotope. This mixture is then applied to a chromatographic medium containing a band or zone of immobilized antibodies to the analyte of interest. When the complex of the molecule to be assayed and the labeled antibody reaches the zone of the immobilized antibodies on the chromatographic medium, binding occurs and the bound labeled antibodies are localized at the zone. This indicates the presence of the molecule to be assayed. This technique can be used to obtain quantitative or semi-quantitative results. Examples of sandwich immunoassays performed on test strips are described by U.S. Pat. No. 4,168,146 to Grubb et al. and U.S. Pat. No. 4,366,241 to Tom et al., both of which are incorporated herein by reference.

In competitive immunoassays, the label is typically a labeled analyte or analyte analogue which competes for binding of an antibody with any unlabeled analyte present in the sample. Competitive immunoassays are typically used for detection of analytes such as haptens, each hapten being monovalent and capable of binding only one antibody molecule. Examples of competitive immunoassay devices are those disclosed by U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

Although useful, currently available immunoassay techniques have a number of disadvantages. For example, because antibodies and other immunoassay reagents are susceptible to environmental conditions, at-home or on-site methods are problematic. Further, antibodies continue to be expensive to produce. Accordingly, it would be advantageous to employ an analyte assay system with all of the advantages of an immunoassay, but which is free of the inherent disadvantages traditionally associated with such immunologically based systems.

In addition to immunoassays, protein-binding assays have been utilized to quantitatively detect various analytes within a sample. These assay systems utilize a protein, such as a protein receptor, which is specific for a particular analyte target. Unfortunately, because these systems utilize the entire protein and the protein may have binding sites for more than one target analyte, there can be problems with cross-reactivity and assay accuracy. For example, in angiotensin II SPA receptor binding assays, the whole angiotensin membrane protein receptor is immobilized on a bead. This bead-receptor complex is then contacted with a sample, binding any angiotensin present in the sample.

Determination of optimum breeding time is important to the success of breeding domestic species. For example, the ability to rapidly and accurately measure equine ovarian steroid hormone estradiol (E2), in the field, would greatly benefit veterinarians in assisting managers of equine breeding farms in making breeding management decisions. The literature is replete with reference to early pregnancy failure in a variety of domestic species, e.g. sheep, 20 to 30% (Edey, 1969; Hanley, 1961; Nancarrow, 1994), goats, 6 to 42% (Kidder et al., 1954; Diskin et al., 1980), pigs, 20 to 30% (Bolet, 1986), cattle, 8 to 42% (Pope et al., 1985) and mares, 15 to 25% (Ginther, 1986; Villahoz et al., 1985; Ball et al., 1986; Ball et al., 1987). A major component of these losses represents errors of fertilization and/or exchange of genetic information (Hunter, 1994; King, 1990) or errors in the interaction between the maternal uterine unit and the developing conceptus (Bazer et al., 1986) even if successful breeding has occurred. With such losses inherent to the reproductive process, it is critical for veterinarians and managers to select the optimal time for breeding to maximize the potential for a successful pregnancy.

Current on-site methods for selecting the optimal time of breeding in the equine industry include the observation of behavioral interactions between the mare and stallion (teasing), rectal palpation and/or ultrasound to monitor ovarian follicular growth, as well as obligatory breed registry regulations. Teasing refers to the observation of the mare's behavior to the presence of a stallion. Distinct behavioral patterns are observed during each phase of the equine estrous cycle (Ginther, 1992). Palpation involves the insertion of the arm into the mare's rectum to manually determine ovarian follicular activity. Often, ultrasound viewing of ovarian follicular activity is also utilized. Accurate record of teasing and palpation/ultrasound data are essential for good breeding management.

Predicting optimal breeding time is also important because the nature of the breeding business adds constraints to successful conception. Most breeders do not keep stallions on their farms, and access to popular stallions requires scheduling and transportation of the mare to the stallion at a predetermined time (reserved booking date/time). This process adds substantial cost and financial risk and, therefore, increases the value of a tool that can predict ovulation. Furthermore, the arbitrary January 1 birth date employed by many breed registries requires that breeding and pregnancy occur as early in the breeding season as possible. Given a gestation length of 340 days, on average (Jeffcoat, 1972), early pregnancy results in birth as early in the following January as possible, creating a more mature, market valuable, horse for sale or training. According to the TBH Market Watch (1997), January foals were sold for 25% more compared to foals born in other months (i.e., February through July).

While predicting optimal breeding time is advantageous, few managers have the skill to accurately perform rectal palpation and even fewer have access to ultrasound. Veterinarians customarily charge managers for each farm visit and for each mare which they have to palpate and/or ultrasound. Moreover, traditional on-site breeding management practices (teasing, rectal palpation and/or ultrasound) cannot determine if a pre-ovulatory sized follicle will ovulate or regress. Accordingly, any technology which would allow the pre-selection of mares which require veterinary attention would be more efficient and economical.

The ovarian steroid hormone estradiol (E2) is a reliable indicator of the time of ovulation in mammals. During the breeding season, E2 is a critical hormone for normal follicular maturation, uterine endometrial development and ovulation in mares, as well as other mammals (Lipner, 1988). Furthermore, E2 exhibits a distinct secretory pattern during the estrous cycle during the breeding season. Mares are seasonal breeders with an annual reproductive cycle consisting of four phases: the breeding season (late spring to summer), the autumnal transition to Anestrus (late summer and fall), Anestrus (winter) and the vernal transition from Anestrus to the breeding season (late winter and spring) (Sharp, 1980). The breeding season is characterized by repeated estrous cycles, providing multiple, successive opportunities to become pregnant. Concentrations of E2 in blood are low (5 to 10 pg/ml) during the diestrus period; increase dramatically (30 to 70 pg/ml) in the 3 to 4 days preceding ovulation; peak 1 day prior to ovulation, on average; then decline to low diestrus concentrations (Pattison et al., 1974). Estrous cyclicity continues until either pregnancy results or declining day length initiates the transition into anestrus. Autumnal transition is not very well characterized. Briefly, a decline in hypothalamic-pituitary support, including GnRH (Strauss et al., 1979), LH and FSH secretion (Ginther, 1992), results in a progressive disruption in ovarian follicular growth and steroid hormone production. Anestrus begins when GnRH secretion reaches low, unvarying levels, LH and FSH secretion cease and ovarian follicular activity ceases (Ginther, 1992). Increasing day length in late winter initiates an increase in GnRH secretion and FSH secretion resulting in increased follicular growth (Ginther, 1992). An average of between 3 and 4 large, pre-ovulatory size follicles develop but fail to ovulate during this period (Tucker et al., 1993). These large, anovulatory follicles create considerable confusion as they are similar to ovulatory follicles in diameter, but they are unaccompanied by an increase in LH and they do not ovulate. Furthermore, these anovulatory follicles do not produce E2. LH secretion and E2 secretion do not recommence until immediately prior to the first ovulation of the year (the start of the breeding season) (Sharp et al., 1997).

Currently, veterinarians and breeding managers can determine E2 levels in mares only by submitting blood samples to a diagnostic laboratory. This process is costly and results are usually not available for 24 hours to one week, depending on the lab. Present commercial assay systems for E2 require several hours of incubation and expensive detection systems. Such assays utilize radioactive substances or hazardous chemicals and complicated procedures, neither of which is compatible with on-site use. For example, U.S. Pat. No. 5,460,976 teaches an luminescence assay for measuring oestradiol in the blood sample of an equine using two antibodies, an antibody against human oestradiol and an antibody against human FSH. Unfortunately, in view of the extreme sensitivity of the immunologic components to both environmental condition and chemical environment, this method also does not lend itself to on-site use. Accordingly, the ability to rapidly and accurately measure E2, in the field, would greatly benefit veterinarians in assisting managers of equine breeding farms in making breeding management decisions.

BRIEF SUMMARY OF THE INVENTION

The subject invention concerns methods and materials for accurately assessing the presence or absence of an analyte of interest in a sample. The LBD is then used to detect the presence of a target analyte in a sample based on binding of the analyte by the LBD. In one embodiment, the subject invention involves utilizing a ligand binding domain (LBD) of a receptor to selectively capture a target analyte that is bound by the LBD. Accordingly, the methods of the invention can be used to detect any target analyte for which there is a receptor molecule having a ligand binding domain that specifically binds the target analyte. In one embodiment, the receptor molecule is a protein or polypeptide.

An exemplified embodiment of the present invention is directed to methods and materials for the rapid detection and quantitation of ovarian steroid hormone estradiol (E2) in the peripheral circulation of mammals, particularly horses. In this embodiment, the LBD utilized is a recombinantly-expressed polypeptide derived from the native equine estrogen receptor (eER) capable of specifically binding E2.

BRIEF DESCRIPTION OF THE DRAWINGS

FIGS. 3A–3F show components and steps of a liquid phase assay of the present invention, wherein estradiol is the analyte of interest.

FIGS. 4A–4E show components and steps of a solid phase assay of the present invention, wherein estradiol is the analyte of interest.

Figure 1:
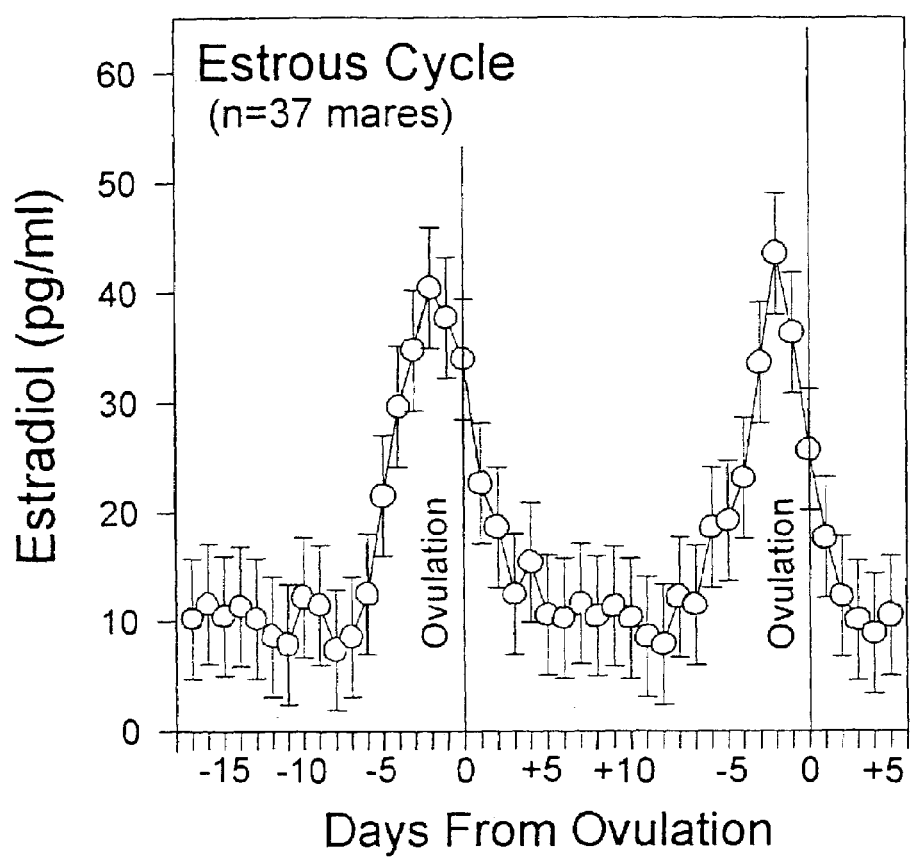
FIG. 1 shows estradiol concentrations (pg/ml) in mares during two consecutive estrous cycles.

BRIEF DESCRIPTION OF SEQUENCE SEQ ID NO:1 is an amino acid sequence of an equine estrogen receptor ligand binding domain according to the present invention.

DETAILED DESCRIPTION OF THE INVENTION

The subject invention concerns methods and materials for accurately assessing the presence or absence of an analyte of interest in a sample, particularly in physiological samples. The methods of the invention utilize a ligand binding domain (LBD) of a receptor molecule that is capable of binding to a target analyte to selectively capture the analyte target specific for that LBD. In one embodiment, the receptor molecule is a protein or polypeptide. The ligand binding domain is allowed to react with a sample and the presence or amount of ligand (i.e., target analyte) bound by the LBD is determined. The subject invention includes within its scope any method or assay in which binding of an LBD to a target analyte can be used for detection or quantitation of the analyte.

The subject invention also concerns the ligand binding domain of the equine estrogen receptor. In an exemplified embodiment, the ligand binding domain has an amino acid sequence of SEQ ID NO:1, or a fragment or variant thereof that retains substantially the same ligand binding affinity as that associated with the polypeptide of SEQ ID NO:1. The subject invention also concerns polynucleotide sequences that encode a ligand binding domain of the present invention.

In one embodiment of the present methods, an LBD is attached to a solid support and contacted with a sample to be assayed for the presence or levels of a target analyte that the LBD specifically binds. After washing, a conjugate comprising target analyte conjugated with a detectable marker, such as an enzyme or radiolabel, is incubated with the LBD on the solid support. Levels of the conjugate bound to the LBD on the support are then determined.

In another embodiment, a sample to be assayed for the presence or level of a target analyte is contacted with a conjugate comprising an LBD for the analyte to be assayed conjugated to a detectable marker, such as an enzyme or a radiolabel. The sample is then contacted with target analyte immobilized to a support matrix, such as SEPHAROSE. After washing, the amount of the LBD-marker conjugate bound to the target analyte on the support matrix is determined.

In a further embodiment, a lateral flow based assay is provided in the present invention for the detection of a target analyte. A sample containing a target analyte of interest is added to an application well in a lateral flow device. The test sample flows toward a zone containing a solid support moiety that has been coated with a ligand-binding domain. When the sample front reaches this zone, the ligand-binding domain attached to the solid support moiety is released from the pad on which they are bound and then allowed to interact with target analyte that may be present in the test sample. Target analyte in the sample binds to the solid support bound LBD and flow continues toward a target analyte affinity matrix. All solid support moieties that possess "unoccupied" LBD are captured by the target analyte affinity matrix, whereas all solid support moieties having fully-occupied LBD will continue toward the capture zone where they are trapped. Results can be assessed visually by colorometric means with the intensity of color being directly proportional to target analyte concentration within the test sample.

The present invention provides a novel approach to analytical methods by utilizing a "capture protein" prepared by genetic engineering of a ligand binding domain of a naturally occurring receptor molecule for a target analyte. The protein from which the LBD is derived has an amino acid sequence which is unique and binds the target analyte specifically. In an exemplified embodiment of an LBD of the present invention, a ligand binding domain portion of a receptor gene for E2 was produced by generating a cDNA fragment coding for the eER ligand binding domain (corresponding to amino acids 301–564 of the full-length receptor protein) by PCR utilizing the eER cDNA plasmid as template. PCR primers which flank the LBD of the eER were designed and synthesized by Gemini Biotech, Ltd. These primers also created XmaI restriction sites for subcloning of cDNA into a pBAD expression vector. Plasmid cDNA was isolated with QIAprep Spin DNA purification columns (Qiagen) and presence of the correct insert size was confirmed by restriction analysis. Following isolation of the eER-LBD subclone, the entire LBD coding region was sequenced to confirm no errors were incorporated by PCR amplification. The eER-LBD peptide was overexpressed in E. coli JM103 cells (available from ATCC, Rockville, Md.) transformed with the pBAD-23-eER-LBD expression vector. Purity of the protein was assessed by SDS-PAGE and Western blot and/or ligand blot analysis.

Use of a genetically engineered LBD as a "capture protein" has several advantages over existing systems. First, the ligand binding domain is specific to the hormone as it represents the naturally occurring tissue receptor mechanisms for recognizing a hormone. Second, use of the ligand binding domain as a "capture protein" is advantageous because the amino acid sequence can be altered by making point mutations in the oligonucleotide primers, and the properties of the ligand binding domain can then be adjusted to suit the needs of an assay system, or other systems requiring hormone-receptor recognition. Third, the in vitro expression of a ligand binding domain assures that a consistent, repeatable source of "capture protein" will be available. Fourth, the ligand binding domain can also be altered to accept organic linker arms for the purpose of attachment to solid phase, or to create attachment points for reporter molecules, such as enzymes, fluorescent molecules or other moities that can indicate the presence of the ligand binding domain having bound target analyte.

While a wide variety of analytes may be assessed utilizing the methods of the invention, the present disclosure exemplifies methods and materials of the invention for the detection of ovarian steroid hormone estradiol (E2). It should be understood, however, that the subject invention is not limited to the detection of estrogens and estradiol. Analytes which can be detected using the methods of the present invention include all those for which a ligand binding domain (LBD) can be derived.

Figure 2:
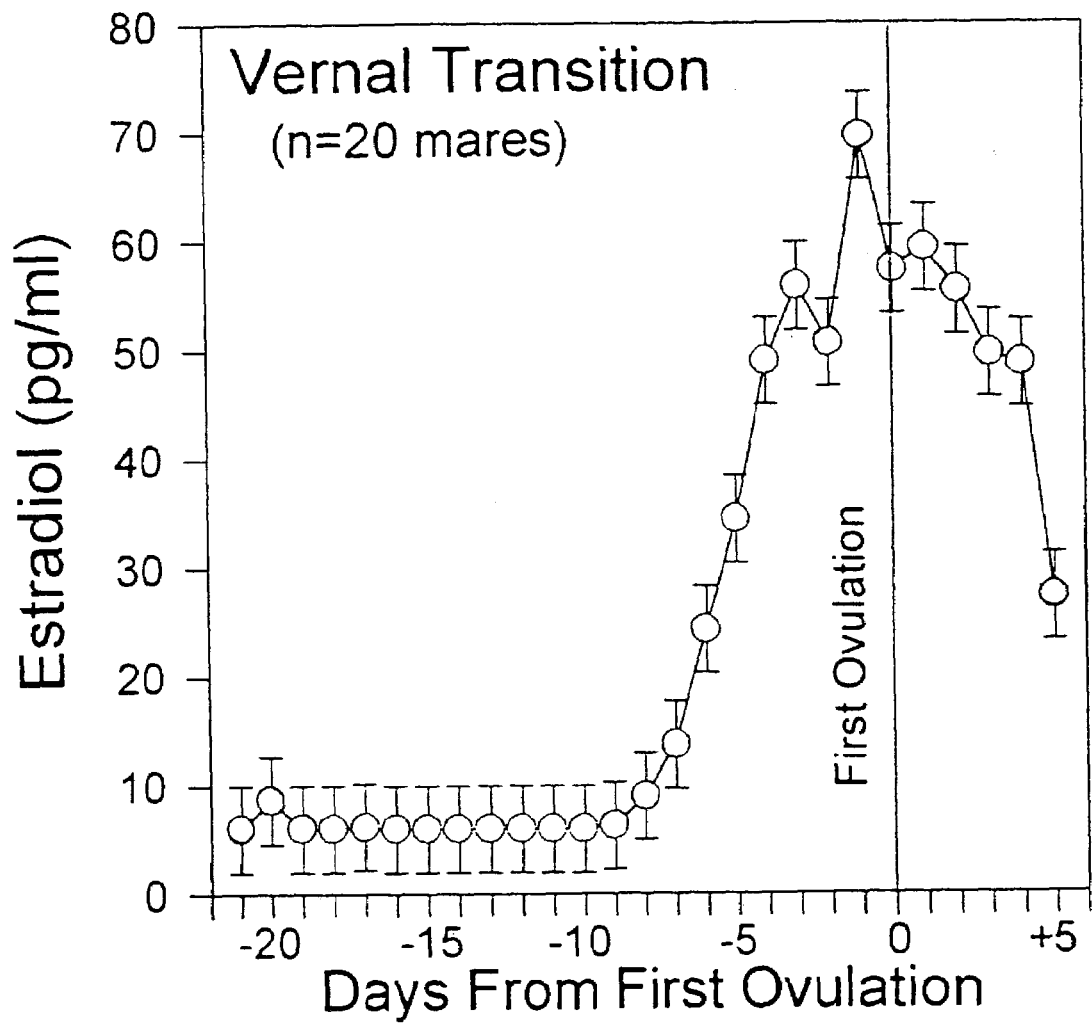
FIG. 2 shows estradiol concentrations (pg/ml) in mares during the vernal transition into the breeding season.

Estradiol levels in mares increase significantly in blood just prior to the first ovulation of the year and just prior to each subsequent ovulation, as shown in FIG. 1. Traditional breeding management practices (teasing, rectal palpation and/or ultrasound) cannot determine if a pre-ovulatory size follicle will ovulate or regress. During vernal transition, E2 synthesis and secretion is very low or absent until the first preovulatory follicle of the year develops, where upon E2 concentrations in blood increase (30 to 70 pg/ml) dramatically (Davis et al., 1990), as shown in FIG. 2.

Figure 3A:
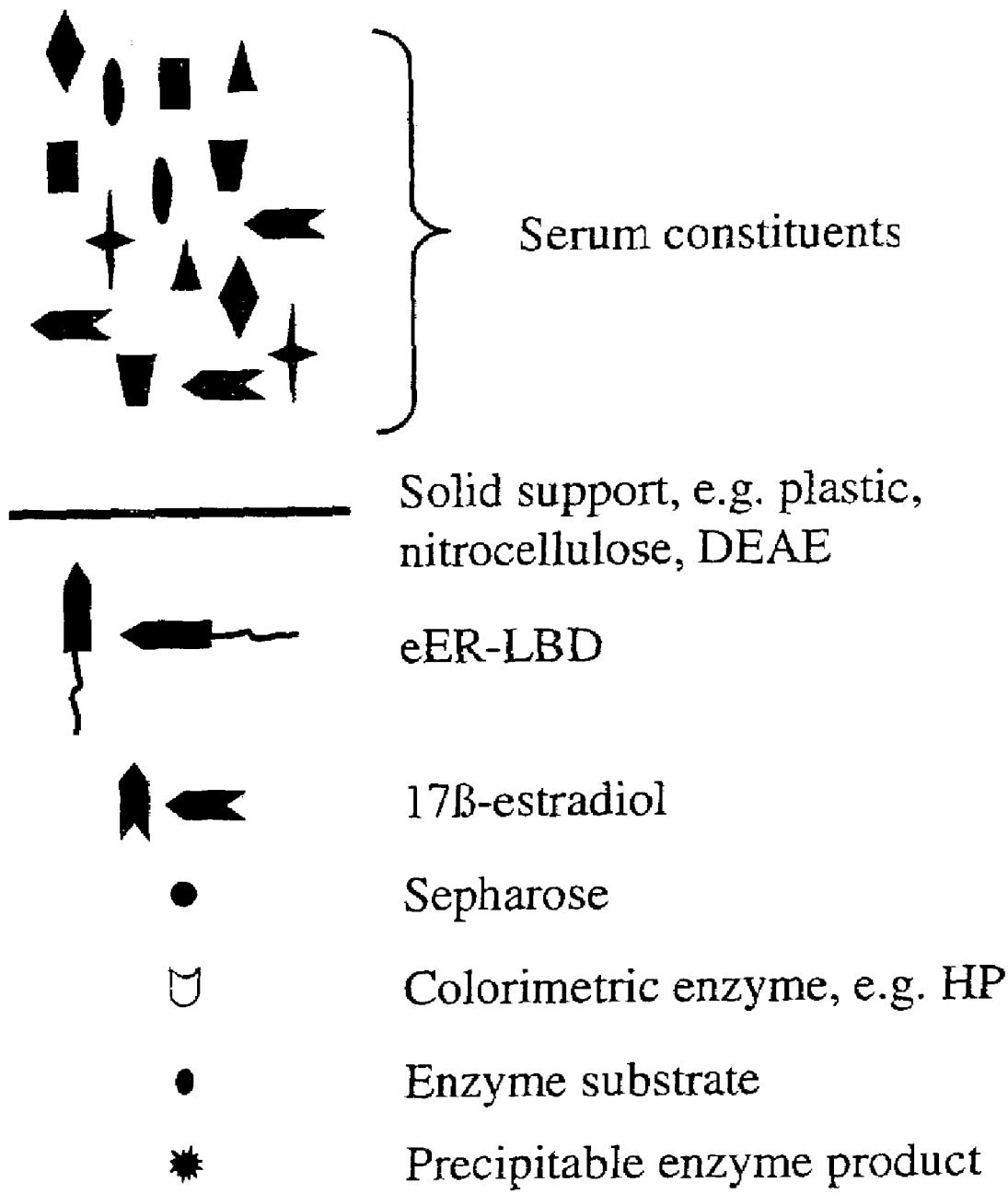
Figure 4A:
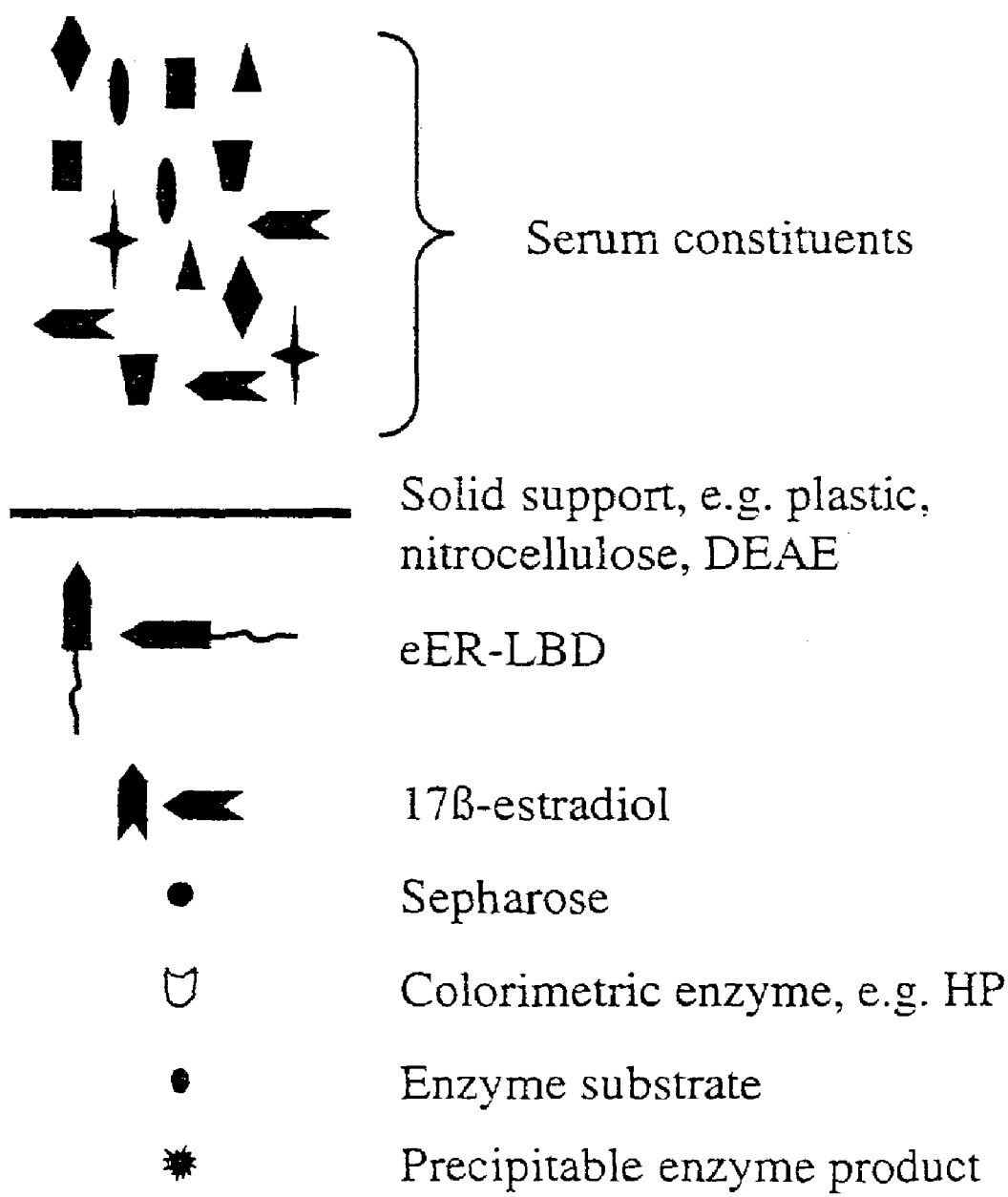
Figure 5A:
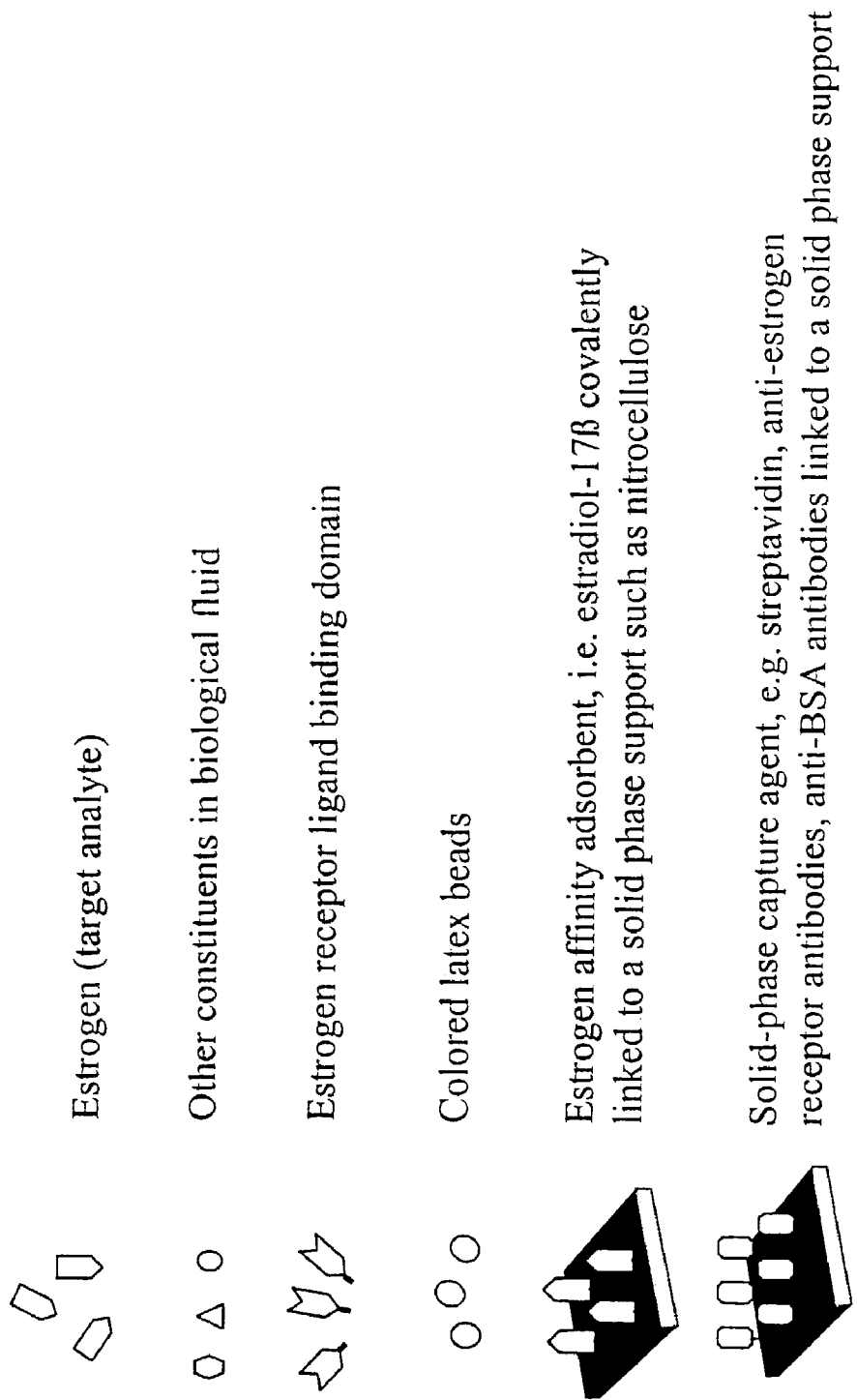
FIGS. 5A–5C show components and steps of a lateral flow-based assay of the present invention, wherein estrogen is the analyte of interest.
Figure 5B:
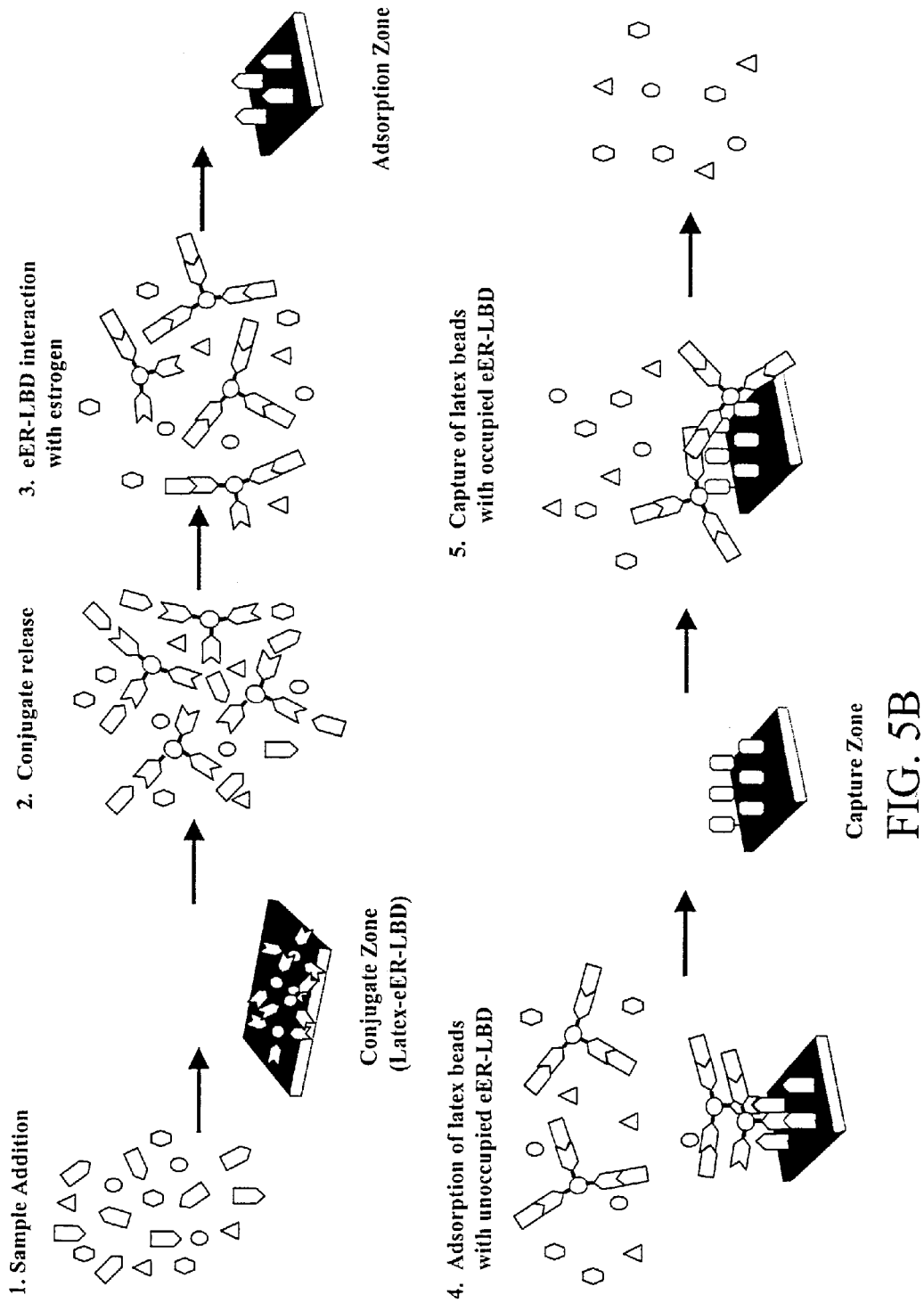
Figure 5C:
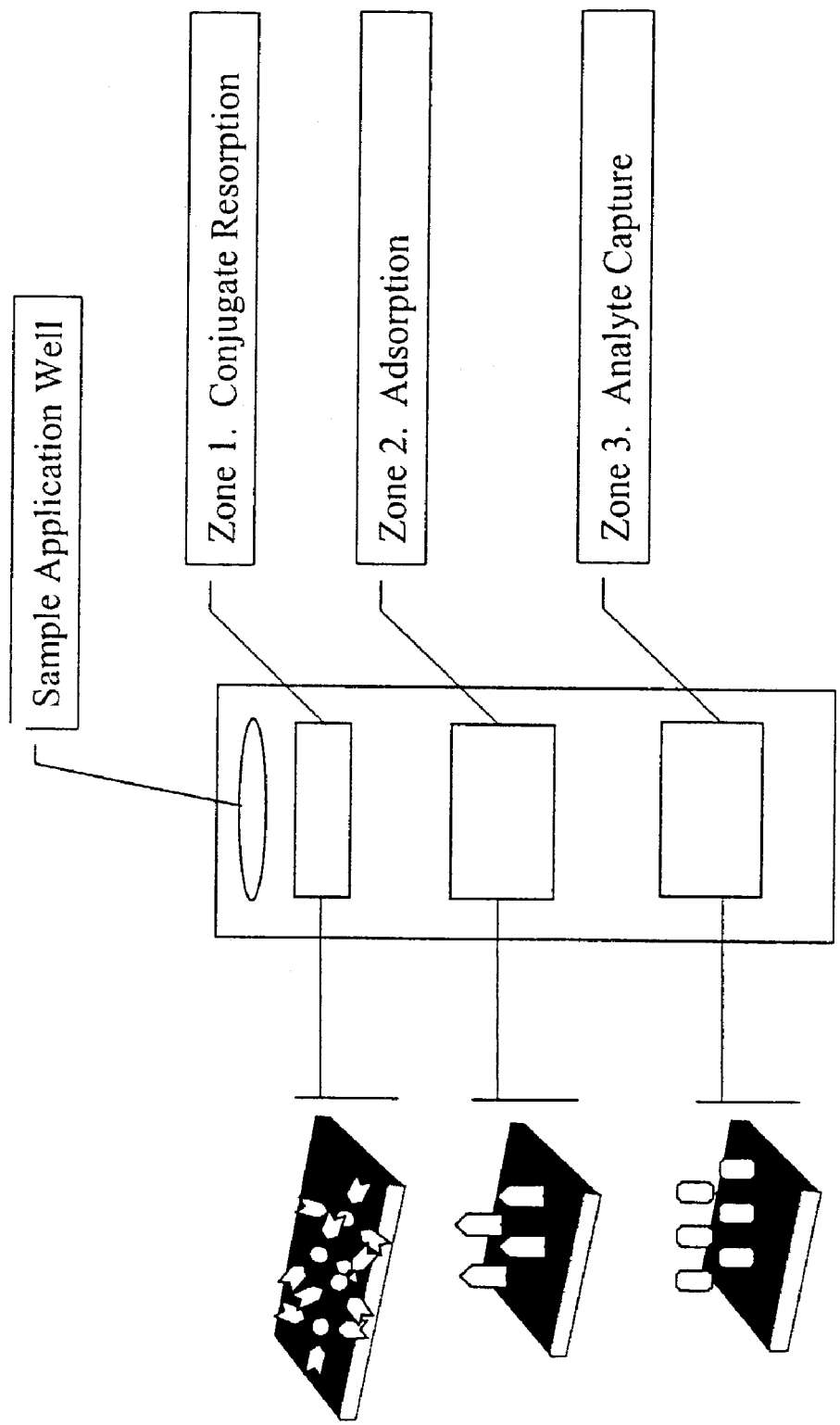

An exemplified embodiment of the present invention provides methods for persons such as veterinarians and breeding managers to determine if a follicle is a "vernal transition (non-ovulatory) follicle," or if the breeding season has begun (i.e., a fertile ovulation can be expected) and thereby make breeding management decisions accordingly. Components for the present methods are shown in FIGS. 3A, 4A and 5A, and included a ligand-binding domain (LBD) of the equine estrogen receptor (eER). Sequence analysis of the LBD of the eER (nucleotide sequence of full-length eER gene: Genbank Assession #AF124093) shows 90% identity and 95% similarity to other mammalian ER-LBDs, as shown in Table 1.

TABLE 1

Comparison of the equine estrogen receptor nucleotide (AF124093) and deduced amino acid sequences to those of other species

| | | Full-length Estrogen Receptor | | | Ligand Binding Domain | |
|---|---|---|---|---|---|---|
| Specie | GenBank Accession | Nucleotide Homology | Amino Acid Identity | Amino Acid Similarity | Amino Acid Identity | Amino Acid Similarity |
| Human | 182192 | 89% | 89% | 93% | 90.5% | 94.9% |
| Mouse | 193180 | 87% | 87% | 91% | 90.5% | 94.9% |

TABLE 1-continued

Comparison of the equine estrogen receptor nucleotide (AF124093) and deduced amino acid sequences to those of other species

| | | Full-length Estrogen Receptor | | | Ligand Binding Domain | |
|---|---|---|---|---|---|---|
| Specie | GenBank Accession | Nucleotide Homology | Amino Acid Identity | Amino Acid Similarity | Amino Acid Identity | Amino Acid Similarity |
| Rat | 56120 | 83% | 86% | 90% | 90.2% | 94.3% |
| Pig | 587554 | 91% | 91% | 94% | 90.5% | 94.6% |
| Cow | 1575521 | ND | ND | ND | 95.0% | 96.0% |
| Sheep | 1617201 | 89% | 90% | 94% | 90.5% | 94.9% |
| Chicken | 63380 | 78% | 76% | 84% | 85.5% | 91.6% |

Published data of all amino acids critical for E2 binding to the ER-LBD in other species (Ekena et al., 1996) are in identical sequence positions in the eER-LBD (Gly$^{521}$, His$^{524}$, Leu$^{525}$, Met$^{528}$). Therefore, the binding kinetics of the eER-LBD should not be different from data published for other species ($K_d$=0.1 nM)(Ekena et al., 1996). Such ER-LBD peptides can be expressed as individual peptides (e.g., residues 301 to 564 of eER) and maintain their specificity for E2 (Wrenn et al., 1993; Ekena et al., 1996).

Hence, it should be readily apparent by those of ordinary skill in the art that the inherent homology in the estrogen receptor nucleotide between mammalian species extends the utility of the subject invention to the diagnostic detection of E2 within mammalian species other than horses. For example, using either a modified or unmodified ER-LBD, the present invention is applicable to detection of ovulation in humans as well, particularly since preovulatory profiles of estrogen in women are even more robust than those in mares.

There are several alternative embodiments of the methods of the present invention that utilize a recombinantly-expressed polypeptide which contains a ligand binding domain (LBD) that can bind an analyte of interest. One embodiment concerns a liquid phase assay, the components for which are shown in FIG. 3A. A second embodiment concerns a solid phase assay, the components for which are shown in FIG. 4A. A third embodiment concerns a lateral flow assay, the components for which are shown in FIG. 5A. For the purpose of example, and as exemplified in the figures, the analyte of interest can be E2, in which case, a polypeptide containing the LBD of the estradiol receptor is used.

An exemplified embodiment of the methods of the present invention concerns a liquid phase-based assay for equine E2 (FIGS. 3B–3F). In the first step, a sample, for example, blood from a mare to be tested is added to a titrated amount of an eER-LBD enzyme conjugate (hereafter referred to as "conjugate"). The conjugate is composed of a recombinantly-expressed LBD of equine estrogen receptor conjugated to a colorimetric enzyme, such as alkaline phosphatase or horseradish peroxidase. Conjugation of the eER-LBD with the colorimetric enzyme can be accomplished using standard methods. Preferably, the conjugate is titrated such that, when incubated with the sample, it will bind a maximum concentration of 30 pg/ml of E2, becoming saturated. The second step of the method consists of incubation to allow ligand binding. The mixture of conjugate and serum is then added to an estrogen affinity matrix. The estrogen affinity matrix functions as an estradiol affinity adsorbent, preferably consisting of a titrated amount of E2 immobilized upon SEPHAROSE (Amersham Pharmacia). The affinity matrix can be prepared by the linkage of estrogen with SEPHAROSE as described by Greene et al. (1980). Briefly, 17α-allylestradiol 3-acetate is prepared by the reaction of estrone with allylmagnesium chloride followed by acetylation of the phenolic group. The 17α-allylestradiol 3-acetate is then converted to the side-chain epoxide by treatment with m-chloroperoxybenzoic acid and then reacted with reduced 2-hydroxy-3-mercapto-n-propyl-SEPHAROSE-6B. Unreacted sulfhydryl groups in the thiopropyl-SEPHAROSE will be blocked by treatment with iodoacetamide.

The affinity matrix is then washed and conjugate which has not bound to E2 within the sample will bind to the immobilized E2 on the affinity matrix and be "captured." However, conjugate which has bound E2 from the sample will flow through the matrix and, hence, not be captured. A color substrate can then be added to the estrogen affinity matrix, binding to the colorimetric enzyme component of any conjugate which has bound to the immobilized E2, as illustrated in FIG. 3. The intensity of the color will depend on the amount of complex "captured." Hence, color development occurs in a manner inversely proportional to analyte (E2) concentration within the sample. For example, if the mare's serum contains low concentrations of E2, an intense color will result, as most or all of the complexes will be captured on the matrix. However, if greater than 30 pg/ml of E2 are in the mare's serum, no color will result, as all the complexes will pass through the matrix without binding to the immobilized E2. While any number of color stages may be used, for unambiguous visualization it is preferable that the conjugate be titrated in such a way that there is a three stage color possibility. For example, where the sample is mare's serum and the analyte of interest is E2, intense color indicates low E2, light color indicates between 5 and 25 pg/ml of E2 and no color indicates greater than 30 pg/ml E2.

While the color development is inversely proportional to the concentration of the analyte (17β-estradiol) in the test sample, to ensure color reactions that are visible to the eye, it should be understood that amplification of the colorimetric signal can be accomplished by using commercially available antibodies to horseradish peroxidase (HP) and alkaline phosphatase (AP). These antibodies can be biotinylated and amplification achieved with enzyme-labeled streptavidin. Alternatively, a sandwich assay which utilizes streptavidin and biotinylated enzyme can be incorporated to achieve maximal amplification.

The E2 can be immobilized onto the surface of the affinity support matrix by any method that affixes the E2 to the support in a substantially irreversible manner, such as where the E2 is covalently bound to the support matrix. Further, E2 can be attached or coupled to numerous other support matrices known in the art using standard methods. Suitable solid-phase support matrices can be composed of nitrocellulose, DEAE, glass, nylon, particulate silica, polystyrene, polyethylene, polyamides, polyacrylamides, polyvinyls, polypropylene, cellulose agarose, dextran or any other suitable material known in the art. The solid support matrix can be in the form of a vessel, a chamber, a dipstick, beads, particles, membranes, or other forms known in the art. Suitable membranes include those composed of nylon, nitrocellulose or polyvinylidenedifluoride (PVDF).

Because many color substrates are commercially available for each colorimetric enzyme and each has its own optimal conditions for color development, there are a variety of color substrates which can be used within the methods of the present invention. Examples include, but are not limited to, p-Nitrophenyl Phosphate (PNPP; yellow), Fast Red (red) and 5-Bromo-4-Chloro-3'-Indolyphosphate (BCIP)/Nitro Blue Tetrazolium Chloride (NBT; black-purple) for the AP conjugates; and, 2,2'-Azinobis [3-ethylbenzothiazoline-6-sulfonic acid]-diammonium salt (ABTS; green), 3,3',5,5'-tetramethylbenzidine dihydrochloride (TMB; blue or yellow) and 3,3'-diaminobenzidine (DAB; brown) for the HP conjugates at the concentrations recommended by their supplier (Sigma Chemical Company and/or Pierce Chemical Company). The substrate which yields the most distinguishable changes in color in parallel to changes in analyte concentrations should be selected. However, stability of the substrate prior to the reaction, solubility of the product and sensitivity will all be considerations for substrate selection as well.

The methods of the present invention are also exemplified by a solid phase assay for detecting an analyte, such as E2 in an female equine (FIGS. 4B–4E). In this embodiment, a titrated concentration of eER-LBD is immobilized onto a support matrix, such as a nylon membrane, dipstick, coated vessel or filtration chamber. The solid support matrix can be composed of any of the materials described for the E2 affinity support matrix. As with the liquid phase embodiment, several concentrations of eER-LBD can be used. Preferably, the optimum titration will be that which is saturated by 30 pg/ml 17β-estradiol.

In the first step of the solid phase embodiment, immobilized (solid phase) eER-LBD is incubated at room temperature with the sample to allow for binding of eER-LBD with 17β-estradiol present in the sample. In the second step of the solid phase embodiment, the sample is then passed or drawn through or evacuated by vacuum filtration through the solid support matrix and the support matrix washed. Optionally, the wash solution can be a buffer that contains a blocking agent (e.g., gelatin or BSA) to reduce nonspecific binding. After the washing/blocking step, a titrated concentration of a 17β-estradiol-enzyme conjugate (hereafter referred to as the estrogen conjugate) is added to the membrane and incubated to allow interaction with the solid-phase eER-LBD that has not bound ligand. As with the liquid phase embodiment, the enzyme of the estrogen conjugate can be a colorimetric enzyme. After incubation, estrogen conjugate which is not bound by eER-LBD is removed and the solid support matrix can be washed. The solid support is then reacted with a substrate for the given enzyme conjugate as previously described in the liquid phase embodiment. The amount of colorimetric enzyme which remains on the solid support is inversely proportional to the amount of 17β-estradiol in the sample. It is preferable to titer the amount of solid-phase eER-LBD in such a way that a three-stage color development scheme will occur as described in the liquid phase embodiment. In addition, although the above described method utilizes a vacuum filtration manifold, the method can be easily adapted to other systems, such as a gravity flow system.

It should be appreciated that a ligand binding domain used in the methods of the present invention can be modified so as to adjust specificity and/or affinity to suit diagnostic needs. For example, a linker arm may be added to the LBD of the mammalian estrogen receptor for conjugation to plastic, enzymes, etc. In addition, the amino acid substituents of the LBD can be modified so as to alter the affinity of the LBD for its associated analyte. For example, mutations in the amino acid sequence of the LBD, such as amino acid substitutions, deletions and/or additions, are contemplated by the present invention.

Further, it should be understood by the ordinarily skilled artisan that the present invention may be further modified to resemble an "antibody sandwich" assay. For the purposes of this disclosure, the term "antibody sandwich" assay simply means an assay in which the analyte to be determined is "sandwiched" by an immunochemical reaction between a solid surface treated with a first antibody reactive with the analyte to be determined and the same or a different second antibody which has been coupled to an enzyme label. This "antibody variant" of the subject invention differs from traditional antibody sandwich assays in that the variant uses one antibody and the LBD of the subject invention, whereas traditional sandwich assays utilize two antibodies. For example, in the aforementioned liquid phase embodiment, a titrated amount of antibodies specific for the eER-LBD are immobilized upon the SEPHAROSE (Amersham Pharmacia) solid support, in lieu of 17β-estradiol. Alternatively, in the solid phase embodiment, an antibody-enzyme conjugate is added instead of the 17β-estradiol-enzyme conjugate. In this variant of the solid phase embodiment, the antibody is specific for the eER-LBD. In both of these antibody-variants of the liquid and solid phase embodiments, the amount of antibody used is titrated as previously described regarding the eER-LBD. Further, monoclonal antibodies may be used in the assays, as disclosed in U.S. Pat. No. 4,376,110.

Additionally, U.S. Pat. No. 4,228,240 describes the stabilization of peroxidase containing compositions for use in enzyme immunoassay kits. U.S. Pat. No. 4,931,385 discloses an improved blocking solution which protects against nonspecific antibody binding and an improved antibody-enzyme conjugate which protects the antibody from loss of reactivity and immunological binding specificity even if the reagents had been subjected to hot, humid environmental conditions. Such reagents may be used in connection with the subject invention.

The methods of the invention can be used to detect any target analyte for which there is a protein that binds to the analyte and for which a ligand binding domain can be derived. Target analytes include analytes such as hormones, enzymes, lipoproteins, bacterial or viral antigens, immunoglobulins, lymphokines, cytokines, drugs, soluble cancer antigens, and the like. These analytes include various proteins such as protamines, histones, phosphorylated proteins, nucleoproteins, such as, for example, transcortin, erythropoietin, transferrin, various globulins, thyroxin-binding globulin, the immunoglobulins of various subclasses (IgA, IgG, IgD, IgE, and IgM), various complement factors, and blood clotting factors such as fibrinogen, Factor VIII, tissue thromboplastin, and thrombin. Further, the relationship of the binding pair (i.e., the target analyte and the protein from which the LBD is derived) is not limited. For example, the relationship may be one of enzyme-substrate, enzyme-inhibitor, enzyme-co-enzyme, etc. In addition to E2, other steroids including, but not limited to, progesterone and testosterone, and other hormones such as insulin, glucagon, relaxin, thyrotropin, somatotropin, luteinizing hormone, follicle-stimulating hormone, gastrin, bradykinin, vasopressin, and various releasing factors are suitable analytes. A wide range of antigenic polysaccharides can also be determined such as those from *Chlamydia, Neisseria gonorrheae, Pasteurella pestis, Shigella dysentereae*, and fungi such as *Mycosporum* and *Aspergillus*. Another major group comprises oligonucleotide sequences which react specifically with protein targets.

The test sample can be any material suspected of containing the analyte of interest. The sample can be derived from any source, such as physiological fluid, including blood, saliva, sweat, urine, milk, mucous, etc. The sample can be used as obtained directly from the source or following a pretreatment so as to modify its character. Pretreatment may involve separating plasma from blood, diluting viscous fluids, or the like. Methods of treatment can involve filtration, distillation, concentration, inactivation of interfering components, and the addition of reagents. For example, the test sample may be dissolved in or supplemented by a buffer to provide a suitable medium for the incubations of the invention. Further, in the case of the antibody variants of the subject invention, an additive may be included to facilitate immunologic reactions involving the antibody.

A further embodiment of the methods of the subject invention utilizes a modification to the lateral flow technique described in U.S. Pat. Nos. 4,943,522; 5,766,961; and 5,770,460. In the first step of this embodiment, a biological sample containing the target analyte of interest (e.g., estrogen) is added to an application well in a lateral flow device. Lateral flow is accomplished by incorporating a non-bibulous support, with inherent hydrophobic properties, which facilitates non-bibulous lateral flow of the test sample to various zones. The test sample flows toward a zone containing colored latex particles that have been coated with eER-LBD. The conjugation of the eER-LBD to latex particles can be by passive adsorption or via a covalent linkage. When the sample front reaches this zone, the colored latex particles are released from the pad from which they are impregnated and allowed to interact with the estrogen (analyte) present in the test sample. Estrogen in the sample binds to the latex bound eER-LBD and flow continues toward an estrogen affinity matrix. All latex particles that possess "unoccupied" eER-LBD are captured by the estrogen adsorbent, while all latex particles with fully-occupied eER-LBD will continue toward the capture zone where they are trapped in a very defined area. The capture zone can utilize a number of high affinity reactions including streptavidin-biotin or antibody-antigen interactions. Results are assessed visually with the number of captured beads, and thus intensity of color, being directly proportional to estrogen concentrations within the test sample (see FIG. 5A). Positive color development for physiological relevant concentrations of analyte is controlled by careful titration of the number of latex beads, the number of eER-LBD sites on each bead and/or the concentration of affinity adsorbent used.

It should be understood by those of ordinary skill in the art that various diagnostic devices usable in connection with other binding assays may be used in connection with the subject invention. For example, U.S. Pat. No. 4,361,537 and U.S. Pat. No. 4,855,240 disclose test devices comprising a highly absorbent material capable of transporting the test sample by capillarity. Further, certain devices rely on improved transverse flow through a filter in order to remove particulate and/or colored matter from the sample which may otherwise interfere with an accurate colorimetric reading, such as that disclosed in U.S. Pat. No. 4,623,461. It should also be appreciated by those of ordinary skill in the art that the present invention may be utilized in a device which uses a plurality of test elements, each for a different analyte, with all elements being supplied analyte from a single quantity of test sample, along different flow paths, as described in U.S. Pat. No. 4,323,536.

In addition, the eER-LBD of the present invention may be modified in order to detect and measure phytoestrogen within mammals, particularly agricultural animals such as horses and cows. Phytoestrogen is of concern to ranchers because phytoestrogen may accumulate in animals that eat plants with high amounts of phytoestrogen. Abnormal levels of phytoestrogen may then result in abnormal changes in the animal's estrous cycles.

All patents, patent applications, provisional applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Cloning of the Equine Estrogen Receptor

The full-length equine estrogen receptor (eER; alpha-type; clone Kjm eER-13) was cloned from an estrous endometrial cDNA library (ZAP EXPRESS; Stratagene) using standard screening procedures (Sambrook et al., 1989). One microgram of eER cDNA plasmid was transformed into DH521 competent cells and plated onto LB-agar. Two independent colonies were picked and selectively grown in 200 ml of Luria-Bertani (LB) culture broth with kanamycin (100 ug/ml ). Equine ER cDNA plasmid was isolated from the growth cultures with the Plasmid Midi Kit (Qiagen). The cDNA insert (>>4000 bp) was sequenced in its entirety by the DNA sequencing core laboratory of the Interdisciplinary Center for Biotechnology Research (ICBR) at the University of Florida. Nucleotide sequence comparisons were performed with the BLAST feature of the National Center for Biotechnology Information, as shown in Table 1. The eER nucleotide sequence was submitted to GenBank and assigned the accession number AF124093.

EXAMPLE 2

PCR Cloning of the eER Ligand Binding Domain

A cDNA fragment coding for the eER ligand binding domain (LBD; amino acids 301–564 based on the amino acid numbering of the full-length receptor sequence at Accession No. GI:4325290) was generated by PCR utilizing th eER cDNA plasmid as template. Oligonucleotides that flank the LBD of the estrogen receptor were designed and synthesized by Gemini Biotech, Ltd. and included XmaI sites at the 5' ends for future subcloning steps. Following 30 cycles of PCR (95° C. for 1 minute, 55° C. for 2 minute, 72° C. for 2 minutes), 10 µl of the PCR reaction was separated on a 1.8% agarose gel to confirm amplification of the correct product size (840 bp). One µl of the PCR reaction was ligated to pCR 2.1 cloning vector (Invitrogen) using the TA cloning principles. The ligation reaction (3 µl) was transformed into One Shot competent cells (Invitrogen) and plated onto LB-kanamycin agar plates that contained X-gal. Ten randomly selected recombinant (white) colonies were selected, inoculated into LB-ampicillin and grown overnight at 37° C. Plasmid cDNA was isolated with QIAprep Spin DNA purification columns (Qiagen) and presence of the correct insert size confirmed by restriction analysis. Following plasmid isolation, the eER-LBD clone was sequenced in its entirety by the DNA sequencing core laboratory of the Interdisciplinary Center for Biotechnology Research (ICBR) at the University of Florida to confirm no errors were incorporated by PCR amplification.

EXAMPLE 3

Subcloning into an Expression Vector

After confirming no errors were generated by PCR and that the coding sequence is in frame, the nucleotide sequence which codes for eER-LBD was released from the pCR 2.1 vector by digesting with XmaI and gel purifed. The eER-LBD coding sequence was then subcloned into a pBAD expression vector which had been modified to include a pectate lyase secretion signal (pBADPL; Gemini Biotech, U.S. Pat. No. 5,576,195). Furthermore, the pBADPL vector added a 6X-histidine tag and a termination codon to the 3' end of the subclone. Five µl of the ligation reaction was transformed into the E.coli strain JM103 (ATCC) that had been rendered competent using $CaCl_2$ (Sambrook et al., 1989). After a 30 minute incubation on ice, cells were heat shocked for 1 minute at 42° C.; then grown for 1 hour at 37° C. in SOC media with shaking (250 rpm). Transformation reactions were plated onto LB-ampicillin plates and grown overnight at 37° C. Twenty single recombinant colonies were inoculated in LB medium containing 100 µg/ml ampicillin and grown overnight at 37° C. Plasmid DNA was isolated with QIAprep Spin DNA purification columns and orientation determined by restriction analysis and/or DNA sequencing. Two clones, one in the correct and one in the reverse orientation (negative control), was utilized for protein expression.

EXAMPLE 4

Recombinant Expression of the eER-LBD Peptide

Initially, pilot studies were conducted to determine optimal conditions for induction. Single recombinant colonies for each clone were selected from LB-ampicillin plates and inoculated into 2 ml of LB containing 100 µg/ml ampicillin. Cultures were grown at 37° C. with shaking (250 rpm) to an $OD_{600}$=1–2. Five 10-ml aliquots of LB-ampicillin were each inoculated with 100 µl of the overnight culture and grown at 37° C. with vigorous shaking to an $OD_{600}$=0.5 (mid-log phase). When an $OD_{600}$=0.5 was obtained, 1 ml of each culture was removed and saved for future analysis (Time 0 h). To the remaining 9 ml of each of the five respective growth cultures, 90 µl of a 10-fold serial dilution of 20% L-arabinose (0.002%–20%) was added such that the final arabinose concentrations ranged from 0.00002%–0.2%. Cultures were grown an additional 4 hours at 37° C. with shaking. One ml aliquots were removed (Time 4 h) and aliquots for both time points were centrifuged at maximum speed in a microfuge for 30 seconds. The supernatant (excreted protein) and the cell pellet (protein secreted into the periplasmic space) were added to Laemmli sample buffer, fractionated on a 12% gel by SDS-PAGE and stained with Coomassie blue. Gels were examined to determine the optimal arabinose concentration for induction as well as the proportion of the protein that is excreted into the medium. Once optimal conditions for maximum expression have been determined, expression can be scaled up accordingly depending upon the yields and the needs.

EXAMPLE 5

Affinity Purification of the Recombinant eER-LBD Peptide

The culture media can be concentrated with Centricon-plus 80 centrifugal filtration devices and dialyzed overnight against binding buffer (20 mM sodium phosphate, 500 mM sodium chloride, pH=7.8) at 4° C. Total protein is determined with the BioRad protein assay. The eER-LBD protein is selected from the media by batch binding to ProBond resin (Invitrogen). An aliquot of the dialyzed media (equivalent to 5 mg of total protein) is brought to a total volume of 10 ml with binding buffer and divided into two 5-ml aliquots. One 5-ml aliquot is batch bound to 5 ml of ProBond resin with gentle rocking for 10 minutes at room temperature. The resin is settled by centrifugation at 800×g and the supernatant decanted. This is repeated with the second 5-ml aliquot. The resin is then washed three times with a native wash buffer (20 mM sodium phosphate, 500 mM sodium chloride, pH=6.0) by resuspending the resin in 10 ml of the wash buffer, rocking for 2 minutes and separating by centrifugation at 800×g. After the final wash, the resin is transferred to a column. The eER-LBD protein is eluted from the resin by consecutively adding 10 ml of each of four imidazole buffers (50 mM, 100 mM, 250 mM, 500 mM), collecting 1 ml fractions and monitoring the $OD_{280}$ of each fraction. Fractions with peak absorbance are pooled and purity is assessed by SDS-PAGE. Protein is quantified with the BioRad protein assay after dialysis to remove the imidazole. Purity of the protein is assessed by SDS-PAGE and Western blot analysis.

EXAMPLE 6

Scatchard Analysis for Estrogen Binding to eER-LBD

After expression and purification, the equilibrium binding affinity of eER-LBD for [$^3$H]17β-estradiol can be determined by saturation analysis. Receptor preparations are diluted in TEDG buffer (10 mM Tris, 1.5 mM EDTA, 1 mM dithiothreitol, 10% vol/vol glycerol; pH 7.8). Dilutions (1–2 nM) of the receptor preparation are then incubated at 4 C overnight with increasing concentrations (0.2–20 nM) of [$^3$H]17β-estradiol. Nonspecific binding is determined in the presence of a 200-fold excess of unlabeled 17β-estradiol. Free ligand is separated from bound ligand by addition of an equal volume of dextran-coated charcoal slurry (1% charcoal, 0.01% dextran in TEDG). After a 10 minute incubation on ice, the charcoal is pelleted by centrifugation for 5 minutes at 14,000 rpm in a microfuge. The supernatent is carefully decanted and a portion used to quantitate [$^3$H]17β-estradiol binding by liquid scintillation counting using SCINTIVERSE cocktail. All data is then transformed by the method of Scatchard (1949) and an equilibrium dissociation constant ($K_d$) determined for the eER-LBD. The calculated $K_d$ value can compare to those of the ER-LBD expressed in other species and by other expression systems.

EXAMPLE 7

Dissociation Kinetics of Estradiol from eER-LBD

The dissociation of [$^3$H]17β-estradiol from the eER-LBD peptide can be measured by the exchange of [$^3$H]17β-estradiol with an excess of unlabeled 17β-estradiol. The eER-LBD peptide (1–2 nM) is incubated with saturating (10 nM) concentrations of [$^3$H]17β-estradiol at 4° C. overnight. Samples are then pre-incubated in a 29° C. waterbath for 30 minutes prior to the addition of a 1000-fold excess of unlabeled 17β-estradiol. Dissociation is allowed to progress at 29° C. and aliquots are removed every 30 minutes for 8 hours. Nonspecific binding is determined by performing the overnight incubation in the presence of a 200-fold excess of unlabeled 17β-estradiol. Dissociation-rate experiments are terminated by DEAE filtration as described by Salomonsson et al. (1993). Briefly, DEAE paper discs (DE 81, Whatman International Ltd) are put into a filtration manifold and the sample is applied to the dry disc. A 2 minute incubation is performed prior to vacuum filtration to allow the eER-LBD-estrogen complex to bind to the filter disc. After vacuum is applied, the discs are washed with 10 volumes of ice-cold Tris buffer (pH 7.8) and transferred to scintillation vials. Radioactivity is allowed to dissolve in the scintillation cocktail for 4 hours before quantitation. Data is then presented as the amount of [$^3$H]17β-estradiol displaced (percent of the initial binding at time 0) as a function of time.

EXAMPLE 8

Stability of the Unoccupied eER-LBD

The stability of the eER-LBD can be determined by measuring the amount of specific [3H]17β-estradiol binding observed after increasing incubation times at 0° C. or 25° C. After a pre-incubation at either 0° C. or 25° C. for 2–24 hours, specific binding is determined as described above. Results are presented as the percentage specific binding relative to the initial binding capacity as a function of time.

EXAMPLE 9

Conjugation of eER-LBD with Colorimetric Enzymes

The eER-LBD peptide can be conjugated with alkaline phosphatase (AP) or horseradish peroxidase (HP) using preactivated enzymes and the EZ-Link conjugation kits according to the manufacturer's recommendations (Pierce Chemical Company). For AP conjugation, maleimide activated AP is reacted with free sulfhydryl (—SH) groups present in the eER-LBD peptide to form a stable thiol ether linkage (Ishikawa et al., 1983). The AP-eER-LBD conjugate is purified by gel filtration chromatography, adjusted to a protein concentration equivalent to 1 nM eER-LBD and utilized for binding studies. For HP conjugation, periodate activated HP is reacted with amine (—NH$_2$) residues present in the eER-LBD peptide to form a covalent amide bond (Imagawa et al., 1982). After conjugation, the linkage is reduced and the activated HP will be quenched with ethanolamine. The HP-eER-LBD conjugate will be purified on a desalting column, adjusted to a protein concentration equivalent to 1 nM eER-LBD.

EXAMPLE 10

Conjugation of 17β-estradiol with Colorimetric Enzymes

The conjugation of 17β-estradiol with either HP or AP can be accomplished a number of different ways including the mixed anhydride method (Munro et al., 1984), the carbodiimide method and the modified carbodiimide method, which uses an activated estradiol ester prepared with N-hydroxysuccinimide (Munro et al., 1988). Preferably, the mixed anhydrid method is utilized. Briefly, a derivative (hemisuccinate or carboxymethyloxime) of 17β-estradiol (Steraloids) and sec-butylchlorocarbonate are dissolved in N,N-dimethylformamide at 0° C. N-methylmorpholine is added to remove hydrochloric acid and form the mixed anhydride. In a separate reaction, enzyme (AP or HP) is dissolved in water and N,N-dimethylformamide is added. The steroid solution that contains the mixed anhydride is gradually added to the enzyme solution at 0° C. The reaction mixture is stirred for 60 minutes at −20° C. then an additional 120 minutes at 0° C. After the incubation, sodium bicarbonate is added and the reaction mixture is dialyzed overnight against distilled water at 4° C. The dialysate is passed over a Sephadex G-25 column and the 17β-estradiol-enzyme conjugate is aliquoted and stored at −20° C.

EXAMPLE 11

Conjugation of Domain F of eER-LBD with Colorimetric Enzymes

A specific conjugation site can be added to the carboxy-terminus of the expressed eER-LBD peptide (Pierce). This is not as desirable, however, since conjugation is 1:1 (enzyme: eER-LBD). Since the expressed peptide can contain not only the LBD (domain E) of the ER but also domain F, tagging the carboxy-terminus does not impede ligand-receptor interactions since crystallographic studies have shown this region is not an integral part of the binding pocket of the estrogen receptor (Tanenbaum et al., 1998).

EXAMPLE 12

Coating Latex Particles with eER-LBD by Passive Adsorption

The recombinant eER-LBD is coated onto surfactant-free polystyrene latex particles (Interfacial Dynamics Corp.) via physical adsorption. Most commercially available latex particles are hydrophobic and, thus, will adsorb proteins strongly and irreversibly via the hydrophobic domains in the proteins. Briefly, 2.5 ml or 1.25 ml of a 4% or 8% solids, respectively, suspension of colored latex particles (e.g. those with sulfate or carboxyl surface functional groups) is diluted to 10 ml with 25 mM 2-[N-Morpholino]ethanesulfonic acid, pH=6.0 (MES). The suspension is then centrifuged at 3,000×g for 20 minutes to sediment the latex particles. The supernatant is decanted and the latex particles re-dispersed in an additional 10 ml of MES. This mixture is centrifuged at 3,000×g to sediment the latex particles; and, the resultant supernatant is discarded and the pellet resuspended in 5 ml of MES to yield a latex suspension of approximately 2% solids. An equal volume of the 2% latex suspension is added to a 1 mg eER-LBD/ml MES solution (assuming latex particle size is 1 μM). The concentration of eER-LBD can be scaled up or down for smaller and larger particle sizes, respectively. The latex particle/eER-LBD mixture is incubated overnight with gentle mixing at room temperature. The unbound eER-LBD is separated from the eER-LBD-labeled latex particles by centrifugation. The supernatant is saved and a protein determination is performed using the Micro BCA Protein Determination Kit (Pierce). The pellet is resuspended in 10 ml of phosphate-buffered saline, pH=7.2 (PBS) and centrifuged to sediment the particles. This washing step is repeated twice for a total of three washes. The final latex pellet is suspended in the original coupling volume (final concentration of 1.0% solids) of PBS amended with 0.1% glycine and 0.1% sodium azide (storage buffer) and stored at 4° C. Glycine will cover any reactive sites on the microsphere surface not occupied by eER-LBD and will ultimately reduce nonspecific binding. The amount of eER-LBD coupled to the latex particles is determined by subtracting the residual protein measured in the supernatant from the original amount added. The binding properties of the eER-LBD-labeled latex particles are assessed as previously described except that bound is separated from free via centrifugation.

EXAMPLE 13

Coating Latex Particles with eER-LBD by Covalent Coupling

Although passive adsorption is the preferred method of coating latex particles, primary amino groups of protein molecules can also be covalently coupled to carboxyl functional groups on the latex particles using a water soluble carbodiimide such as 1-ethyl-3-(3-dimethyl amino propyl) carbodiimide-HCl (EDAC). Latex suspensions are brought to 2% solids as described above for passive adsorption. This procedure will work with either carboxyl latex or carboxylate-modified latex (CML). To the latex, 2 ml of EDAC in MES (50 mg/ml) and 3 ml of eER-LBD (approximately 5 mg of protein) is added. The latex/protein mixture is incubated at room temperature for 3–4 hours on a rocking platform. Unbound eER-LBD is removed by centrifugation and the supernatant retained for protein determination. The eER-LBD-labeled latex particles is washed 3 times in PBS and resuspended to 1% solids in storage buffer and stored at 4° C. until used to characterize binding properties as previously described except that bound is separated from free via centrifugation.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Pat. No. 5,460,976
U.S. Pat. No. 5,576,195
U.S. Pat. No. 4,376,110
U.S. Pat. No. 4,228,240
U.S. Pat. No. 4,931,385
U.S. Pat. No. 4,943,522
U.S. Pat. No. 5,766,961
U.S. Pat. No. 5,770,460
U.S. Pat. No. 4,361,537
U.S. Pat. No. 4,855,240
U.S. Pat. No. 4,623,461
U.S. Pat. No. 4,323,536

Ball, B. A., T. V. Little, R. B. Hillman, G. L. Woods (1986) "Pregnancy rates at days 2 and 14 and estimated embryonic loss rates prior to day 14 in normal and subfertile mares" *Theriogenology* 26:611–619.

Ball, B. A., G. L. Woods (1987) "Embryonic loss and early pregnancy loss in the mare" *Compendium Equine* 9:459–469.

Bazer, F. W., J. L. Vallet, R. M. Roberts, D. C. Sharp, W. W. Thatcher (1986) "Role of conceptus secretory products in establishment of pregnancy" *J. Reprod. Fert.* 76(2):841–850.

Bolet, G. (1986) "Timing and extent of embryonic mortality in pigs, sheep and goats: Genetic variability" In: *Embryonic Mortality in Farm Animals*, J. M. Sreenan and M. G. Diskin, eds. (Martinus Nijhoff, Dordrecht), pp. 12–45.

Bradford, M. M. (1976) "A rapid and sensitive method for the quantitation of microgram quantities of protein utilizing the principle of protein-dye binding" *Anal. Biochem.* 72:248–254.

Davis, S. D., D. C. Sharp (1991) "Intrafollicular and peripheral steroid characteristics during vernal transition in the pony mare" *J. Reprod. Fertil. Suppl.* 44:333–340.

Diskin, M. G., J. M. Sreenan (1980) "Fertilization and embryonic mortality rates in beef heifers after artificial insemination" *J. Reprod. Fertil.* 59(2):463–468.

Edey, T. N. (1969) "Prenatal mortality in sheep: A review" *Anim. Breed Abst.* 37:173–190.

Ekena, K., K. E. Weist, J. A. Katzenellenbogen, B. S. Katzenellenbogen (1996) "Identification of amino acids in the hormone binding domain of the human estrogen receptor important in estrogen binding" *J. Biol. Chem.* 271(33):20053–20059.

Ginther, O. J. (1986) *Ultrasonic Imaging and Reproductive Events in the Mare.* Equiservices, Cross Plains, Wis.

Ginther, O. J. (1992) "Sexual Behavior" In: Reproductive Biology in the Mare, McNaughton and Gunn, Ann Arbor, Mich.

Greene, G., C. Nolan, J. Engler, E. Jensen (1980) "Monoclonal antibodies to human estrogen receptor" *Proc. Natl. Acad. Sci. USA* 77(9):5115–5119.

Hanly, S. (1961) "Prenatal mortality in farm animals" *J. Reprod. Fertil.* 2:182–194.

Hunter, M. G. (1989) "Characteristics and cause of the inadequate corpus luteum" *J. Reprod. Fertil. Suppl.* 43:91–99.

Imagawa, M., S. Yoshitaki, Y. Hamaguchi, E. Ishikawa, Y. Niitsu, I. Urushizawa, R. Kanazawa, S. Tachibani, N. Nakazawa (1982) "Characteristics and evaluation of antibody-horseradish peroxidase conjugates prepared by using a maleimide compound, glutaraldehyde and periodate" *J. Appl. Biochem.* 4:41–57.

Ishikawa, E., M. Imagawa, S. Hashida, S. Yoshitake, Y. Hamaguchi, T. Ueno (1983) "Enzyme-labeling of antibodies and their fragments for enzyme immunoassay and immunohistochemical staining" *J. Immunoassay* 4:209–227.

Jeffcott, L. B. (1972) "Observations on parturition in crossbred pony mares" *Equine Vet. J.* 4:209–216.

Kidder, H. E., W. G. Black, J. N. Wiltbank, L. C. Ulberg, L. E. Cassida (1954) "Fertilization rates and embryonic death rates in cows bred to bulls of different levels of fertility" *J. Dairy Sci.* 37:691–697.

King, W. A. (1990) "Chromosome abnormalities and pregnancy failure in domestic animals" *Adv. Vet Sci. Comp. Med.* 34:229–250.

Lipner, H. (1988) "Mechanism of mammalian ovulation" In: *The Physiology of Reproduction*, E. Knobil and J. D. Neill, eds. (Raven Press, New York), pp. 447–476.

Munro, C. J., G. Stabenfeldt (1984) "Development of a microtitre plate enzyme immunoassay for the determination of progesterone" *J. Endocrin.* 101 (1):41–49.

Munro, C. J., B. L. Lasley (1988) "Non-radiometric methods for immunoassay of steroid hormones" In: *Non-radiometric Assays: Technology and Application in Polypeptide and Steroid Hormone Detection*, B. D. Albertson and F. P. Haseltine, eds. (Alan R. Liss, Inc., New York), pp. 289–329.

Nancarrow, C. D. (1994) "Embryonic mortality in the ewe and doe" In: *Embryonic Mortality in Domestic Species*, M. T. Zavy and R. D. Geisert, eds. (CRC Press, Boca Raton, Fla.), pp. 79–90.

Pattison, M. L., C. L. Chen, S. T. Kelley, G. W. Brandt (1974) "Luteinizing hormone and estradiol in peripheral blood of mares during estrous cycle" *Biol. Reprod.* 11(3): 245–250.

Pope, W. F., N. L. First (1985) "Factors affecting the survival of pig embryos" *Theriogenology* 23:91–105.

Salomonsson, M., J. Haggblad, B. W. O'Malley, G. M. Sitbon (1994) "The human estrogen receptor hormone binding domain dimerizes independently of ligand activation" *J. Steroid Biochem. Molec. Biol.* 48(5–6):447–452.

Sambrook, J., E. F. Fritsch, T. Maniatis (1989) *Molecular Cloning: A Laboratory Manual,* 2d Edition, Cold Spring Harbor Laboratory Press, Cold Spring Harbor, N.Y.

Scatchard, G. (1949) "The attractions of proteins for small molecules and ions" *Ann. NY Acad. Sci.* 51:660–672.

Seielstad, D. A., K. E. Carlson, J. A. Katzenellenbogen, P. J. Kushner, G. L. Greene (1995) "Molecular characterization by mass spectrometry of the human estrogen receptor ligand-binding domain expressed in *Eschericia coli*" *Mol. Endocrinol.* 9(6):647–658.

Sharp, D. C., G. Robinson, B. D. Cleaver, M. B. Porter (1997) "Role of photoperiod in regulating reproduction in mares: basic and practical aspects" In: *Current Therapy in Large Animal Theriogenology*, R. S. Youngquist, ed. (WB Saunders, Philadelphia, Pa.), pp. 71–78.

Strauss, S. S., C. L Chen, S. P. Kalra, D. C. Sharp (1979) "Localization of gonadotropin-releasing hormone (GnRH) in the hypothalamus of ovariectomized pony mares by season" *J. Reprod. Fertil. Suppl.* 27:123–129.

Tanenbaum, D. M., Y. Wang, S. P. Williams, P. B. Sigler (1998) "Crystallographic comparison of the estrogen and progesterone receptor's ligand binding domains" *Proc. Natl. Acad. Sci. USA* 95(11):5998–6003.

TBH Market Watch. Foaling Dates. Aug. 21, 1997. pp. 11–13.

Tucker, K. E., B. D. Cleaver, D. C. Sharp (1993) "Does resumption of follicular estradiol synthesis during vernal transition in mares involve a shift in steroidogenic pathways?" *Biol. Reprod. Suppl.* 48:188.

Villahoz, M. D., E. L. Squires, J. L. Voss, R. K. Shideler (1985) "Some observations on early embryonic death in mares" *Theriogenology* 23:915–924.

Wrenn, C. K., B. S. Katzenellenbogen (1993) "Structure-function analysis of the hormone binding domain of the human estrogen receptor by region-specific mutagenesis and phenotypic screening in yeast" *J. Biol. Chem.* 268 (32):24089–24098.

---

We claim:

1. An isolated ligand binding domain of an equine estrogen receptor molecule that can bind to a target analyte specific for said ligand binding domain, wherein said ligand binding domain consists of the amino acid sequence of SEQ ID NO:1.

* * * * *